United States Patent [19]
Di Cosimo et al.

[11] Patent Number: 6,066,490
[45] Date of Patent: May 23, 2000

[54] NITRILASE-PRODUCING ACIDOVORAX FACILIS

[75] Inventors: Robert Di Cosimo, Rockland, Del.; Robert Donald Fallon, Elkton, Md.; John Edward Gavagan; Frank Edward Herkes, both of Wilmington, Del.

[73] Assignee: E. I. du Pont de Nemours & Company, Wilmington, Del.

[21] Appl. No.: 08/987,938

[22] Filed: Dec. 10, 1997

Related U.S. Application Data

[62] Division of application No. 08/650,073, May 17, 1996, Pat. No. 5,858,736.

[51] Int. Cl.⁷ .............................. C12N 1/12; C12N 9/78
[52] U.S. Cl. ...................... 435/252.1; 435/253.3; 435/227; 435/128
[58] Field of Search ............................ 435/252.1, 253.3, 435/227, 128

[56] References Cited

FOREIGN PATENT DOCUMENTS

| | | |
|---|---|---|
| 0 178 106 A2 | 4/1986 | European Pat. Off. . |
| 0 444 640 A2 | 9/1991 | European Pat. Off. . |
| 0 481 351 A2 | 4/1992 | European Pat. Off. . |
| 1 171 323 | 1/1959 | France . |
| 1 226 354 | 7/1960 | France . |
| 2 463 126 | 2/1981 | France . |

OTHER PUBLICATIONS

Bargar et al., Rapid and Efficient Method for Dehydration of Primary Amides to Nitriles, *Chemical Abstracts,* 94, No. 3, Abstract No. 14593, Jan. 19, 1981.

M. Cushman et al., A Synthesis of 2–alkyl and 2–benzyl Substituted Acrylonitriles from 2–alkyl and 2–benzylidenecyanoacetate Esters under Mild Conditions, *Chemical Abstract,* 113, No. 25, Abstracts No. 230773.

J. Lange et al., Direct Pyradazine Ring Synthesis from Beta–cyano Esters, *Chemical Abstracts,* 119, No. 21, Abstract No. 225898, Nov. 22, 1993.

*Primary Examiner*—Leon B. Lankford, Jr.

[57] ABSTRACT

A process for the preparation of five-membered or six-membered ring lactams from aliphatic $\alpha,\omega$-dinitriles has been developed. In the process an aliphatic $\alpha,\omega$-dinitrile is first converted to an ammonium salt of an $\omega$-nitrilecarboxylic acid in aqueous solution using a catalyst having an aliphatic nitrilase (EC 3.5.5.7) activity, or a combination of nitrile hydratase (EC 4.2.1.84) and amidase (EC 3.5.1.4) activities. The ammonium salt of the $\omega$-nitrilecarboxylic acid is then converted directly to the corresponding lactam by hydrogenation in aqueous solution, without isolation of the intermediate $\omega$-nitrilecarboxylic acid or $\omega$-aminocarboxylic acid. When the aliphatic $\alpha,\omega$-dinitrile is also unsymmetrically substituted at the $\alpha$-carbon atom, the nitrilase produces the $\omega$-nitrilecarboxylic acid ammonium salt resulting from hydrolysis of the $\omega$-nitrile group with greater than 98% regioselectivity, thereby producing only one of the two possible lactam products during the subsequent hydrogenation. A heat-treatment process to select for desirable regioselective nitrilase or nitrile hydratase activities while destroying undesirable activities is also provided.

1 Claim, No Drawings

NITRILASE-PRODUCING ACIDOVORAX FACILIS

This is a division of application Ser. No. 08/650,073 filed May 17, 1996, which issued as U.S. Pat. No. No. 5,858,736 on Jan. 12, 1999.

BACKGROUND OF THE INVENTION

1. Field of the Invention

This invention relates to a process for the preparation of five-membered or six-membered ring lactams from aliphatic α,ω-dinitriles by a combination of biological and chemical techniques. More particularly, an aliphatic α,ω-dinitrile is first converted to an ammonium salt of an ω-nitrilecarboxylic acid in aqueous solution using a catalyst having an aliphatic nitrilase (EC 3.5.5.7) activity, or a combination of nitrile hydratase (EC 4.2.1.84) and amidase (EC 3.5.1.4) activities. The ammonium salt of the ω-nitrilecarboxylic acid is then converted directly to the corresponding lactam by hydrogenation in aqueous solution, without isolation of the intermediate ω-nitrilecarboxylic acid or ω-aminocarboxylic acid. When the aliphatic α,ω-dinitrile is also unsymmetrically substituted at the α-carbon atom, the nitrilase produces the ω-nitrilecarboxylic acid ammonium salt resulting from hydrolysis of the ω-nitrile group with greater than 98% regioselectivity, thereby producing only one of the two possible lactam products during the subsequent hydrogenation.

2. Description of the Related Art

Nitriles are readily converted to the corresponding carboxylic acids by a variety of chemical processes, but these processes typically require strongly acidic or basic reaction conditions and high reaction temperatures, and usually produce unwanted byproducts and/or large amounts of inorganic salts as unwanted byproducts. Processes in which enzyme-catalyzed hydrolysis convert nitrile substrates to the corresponding carboxylic acids are often preferred to chemical methods, since these processes are often run at ambient temperature, do not require the use of strongly acidic or basic reaction conditions, and do not produce large amounts of unwanted byproducts. An additional advantage of the enzyme-catalyzed hydrolysis of nitriles over chemical hydrolysis is that, for the hydrolysis of a variety of aliphatic or aromatic dinitriles, the enzyme-catalyzed reaction can be highly regioselective, where only one of the two nitrile groups is hydrolyzed to the corresponding carboxylic acid ammonium salt.

A nitrilase enzyme directly converts a nitrile to the corresponding carboxylic acid ammonium salt in aqueous solution without the intermediate formation of an amide. The use of aromatic nitrilases for the hydrolysis of aromatic nitriles to the corresponding carboxylic acid ammonium salts has been known for many years, but it is only recently that the use of aliphatic nitrilases have been reported. Kobayashi et al. (*Tetrahedron,* (1990) vol. 46, 5587–5590; *J. Bacteriology,* (1990), vol. 172, 4807–4815) have described an aliphatic nitrilase isolated from *Rhodococcus rhodochrous* K22 which catalyzed the hydrolysis of aliphatic nitriles to the corresponding carboxylic acid ammonium salts; several aliphatic α,ω-dinitriles were also hydrolyzed, and glutaronitrile was converted to 4-cyanobutyric acid ammonium salt with 100% molar conversion using resting cells as catalyst. A nitrilase from *Comamonas testosteroni* has been isolated which can convert a range of aliphatic α,ω-dinitriles to either the corresponding ω-nitrilecarboxylic acid ammonium salt or the dicarboxylic acid diammonium salt (Canadian patent application CA 2,103,616 (1994/02/11); S. Lévy-Schil, et al., *Gene,* (1995), vol. 161, 15–20); for the hydrolysis of adiponitrile, a maximum yield of 5-cyanovaleric acid ammonium salt of ca. 88% was obtained prior to complete conversion of the 5-cyanovaleric acid ammonium salt to adipic acid diammonium salt.

M. L. Gradley and C. J. Knowles (*Biotechnology Lett.,* (1994), vol. 16, 41–46) have reported the use of suspensions of *Rhodococcus rhodochrous* NCIMB 11216 having an aliphatic nitrilase activity for the hydrolysis of several 2-methylalkylnitriles. Complete conversion of (+/−)-2-methylbutyronitrile to 2-methylbutyric acid ammonium salt was obtained, while the hydrolysis of (+/−)-2-methylhexanenitrile appeared to be enantiospecific for the (+)-enantiomer. C. Bengis-Garber and A. L. Gutman (*Appl. Microbiol. Biotechnol.,* (1989), vol. 32, 11–16) have used *Rhodococcus rhodochrous* NCIMB 11216 as catalyst for the hydrolysis of several dinitriles. In this work, fumaronitrile and succinonitrile were converted to the corresponding ω-nitrilecarboxylic acid ammonium salts, while glutaronitrile, adiponitrile, and pimelonitrile were converted to the corresponding dicarboxylic acid diammonium salts.

A combination of two enzymes, nitrile hydratase (NHase) and amidase, can be also be used to convert aliphatic nitriles to the corresponding carboxylic acid ammonium salts in aqueous solution. Here the aliphatic nitrile is initially converted to an amide by the nitrile hydratase and then the amide is subsequently converted by the amidase to the corresponding carboxylic acid ammonium salt. A wide variety of bacterial genera are known to possess a diverse spectrum of nitrile hydratase and amidase activities, including Rhodococcus, Pseudomonas, Alcaligenes, Arthrobacter, Bacillus, Bacteridium, Brevibacterium, Corynebacterium, and Micrococcus. Both aqueous suspensions of these microorganisms and the isolated enzymes have been used to convert nitriles to amides and carboxylic acid ammonium salts.

P. Hönicke-Schmidt and M. P. Schneider (*J. Chem. Soc., Chem. Commun.,* (1990), 648–650) have used immobilized Rhodococcus sp. strain CH 5 to convert nitriles and dinitriles to carboxylic acid ammonium salts and ω-nitrilecarboxylic acid ammonium salts, respectively. The cells contain both a nitrile hydratase and amidase activity which converts glutaronitrile to 4-cyanobutyric acid ammonium salt in 79% isolated yield based on 92% conversion of substrate. A. J. Blakely et al. (*FEMS Microbiology Lett.,* (1995), vol. 129, 57–62) have used the nitrite hydratase and amidase activity of suspensions of Rhodococcus AJ270 to regiospecifically hydrolyze malononitrile and adiponitrile to produce only the corresponding ω-nitrilecarboxylic acid ammonium salts. H. Yamada et al. (*J. Ferment. Technol.,* (1980), vol. 58, 495–500) describe the hydrolysis of glutaronitrile to a mixture of 4-cyanobutyramide, 4-cyanobutyric acid, glutaric acid and ammonia using Pseudomonas sp. K9, which contains both a nitrite hydratase and amidase. K. Yamamoto et al. (J. Ferment. Bioengineering, 1992, vol. 73, 125–129) described the use of Corynebacterium sp. CH 5 cells containing both a nitrite hydratase and amidase activity to convert trans-1,4-dicyanocyclohexane to trans-4-cyanocyclohexanecarboxylic acid ammonium salt in 99.4% yield.

J. L. Moreau et al. (*Biocatalysis,* (1994), vol 10. 325–340) describe the hydrolysis of adiponitrile to adipic acid, adipamide, and adipamic acid through the intermediate formation of 5-cyanovaleric acid using Brevibacterium sp. R312 (nitrite hydratase and amidase activity). A. Kerridge et al. (*Biorg. Medicinal Chem.,* (1994), vol. 2, 447–455) report the use of Brevibacterium sp. R312 (nitrite hydratase and amidase activity) to hydrolyze prochiral 3-hydroxyglutaronitrile derivatives to the corresponding (S)-cyanoacid ammonium salts. European Patent 178,106 B 1 (Mar. 31, 1993) discloses selective transformation of one of the cyano groups of an aliphatic dinitrile to the corresponding carboxylic acid, amide, ester or thioester using the mononitrilase activity (defined as either nitrilase or a combination of nitrite hydratase/amidase) derived from Bacillus, Bacteridium, Micrococcus or Brevibacterium. In addition to the many examples of bacterial catalysts having nitrilase activity or nitrite hydratase/amidase activity, Y. Asano et al. (*Agric. Biol. Chem.,* (1980), vol. 44, 2497–2498) demonstrated that the fungus *Fusarium merismoides* TG-1 hydrolyzed glutaronitrile to 4-cyanobutyric acid ammonium salt, and 2-methylglutaronitrile to 4-cyanopentanoic acid ammonium salt.

No prior art has been found which describes the hydrogenation of ammonium salts of aliphatic ω-nitrilecarboxylic acids in aqueous solution to directly produce the corresponding lactams. In closely related art, U.S. Pat. No. 4,329,498 describes the hydrogenation of muconic acid mononitrile to 6-aminocaproic acid (6-ACA) in dry ethanol saturated with ammonia, using a Raney nickel catalyst #2. After removal of the hydrogenation catalyst, heating the ethanolic solution of 6-ACA to 170° C.–200° C. was expected to result in the cyclization of 6-ACA to caprolactam. The reductive cyclization of either β-quinoxalinylpropanoic acids (E. C. Taylor et al., *J. Am. Chem. Soc.,* (1965), vol. 87, 1984–1990), or the related 2-(2-carboxyethyl)-3(4H)-quinoxalone (E. C. Taylor et al., *J. Am. Chem. Soc.,* (1965), vol. 87, 1990–1995) by hydrogenation in 1 N sodium hydroxide solution using Raney nickel as the catalyst has been reported to produce the corresponding five-membered ring lactams, but only after removal of the catalyst from the product mixture and acidification of the resulting filtrate. The authors state that for any of these reductions, "lactam formation can only proceed in acidic solution" (page 1992, second paragraph), presumably requiring the presence of the protonated carboxylic acid and not the carboxylate salt. U.S. Pat. No. 4,730,040 discloses a process for the preparation of caprolactam, reacting an aqueous solution of 5-formylvaleric acid with ammonia and hydrogen in the presence of a hydrogenation catalyst, following which ammonia is separated from the product mixture and the resulting solution of 6-ACA is heated to 300° C.

Previous work has disclosed single cells containing both nitrile hydratase and amidase activities that have been used to convert nitriles and dinitriles to various acid ammonium salts. However, no prior art has been found which describes the cyclization of ammonium salts of aliphatic ω-aminocarboxylic acids under the hydrogenation reaction conditions of the present invention (i.e., in an aqueous solution containing an excess of added ammonium hydroxide) to produce the corresponding lactams. In closely related art, the cyclization of aliphatic ω-aminocarboxylic acids (but not the ammonium salts) to the corresponding lactams under a variety of reaction conditions has been reported. F. Mares and D. Sheehan (*Ind. Eng. Chem. Process Des. Dev.,* (1978), vol. 17, 9–16) have described the cyclization of 6-aminocaproic acid (6-ACA) to caprolactam using water or ethanol as solvent. In water, the cyclization reaction was reversible at concentrations below 1 mol/kg (ca. 1 M), and the concentration of caprolactam increased with increasing temperature; at a total concentration of 6-ACA and caprolactam of 0.85 mol/kg (ca. 0.85 M), the percentage of caprolactam was reported to increase from 38.7% at 180° C. to 92.2% at 250° C. In ethanol, a 98% yield of caprolactam was obtained at 200° C., reportedly due to a shift in the equilibrium which favors the free-acid/free-amine form of 6-ACA in ethanol, rather than the intramolecular alkylammonium carboxylate form of 6-ACA which predominates in water. A process for the production of caprolactam from 6-ACA is also described in U.S. Pat. No. 4,599,199, where 6-ACA is introduced into a fluidized alumina bed in the presence of steam at from 290° C. to 400° C. The synthesis of five-, six- and seven-membered ring lactams by cyclodehydration of aliphatic ω-aminoacids on alumina or silica gel in toluene, and with continuous removal of the water produced during the reaction, has been reported by A. Bladé-Font (*Tetrahedron Letters,* (1980), vol. 21, 2443–2446). A free amino group (unprotonated) was reported to be necessary for cyclodehydration to take place.

No prior art has been found which describes the hydrogenation of ammonium salts of aliphatic ω-nitrilecarboxylic acids in aqueous solution containing methylamine to directly produce the corresponding N-methyl lactams. In closely related art, 1,5-dimethyl-2-pyrrolidinone was prepared by the hydrogenation of an aqueous solution of levulinic acid and methylamine in water using a Raney nickel catalyst at 140° C. and 1000–2000 psig of hydrogen R. L. Frank et al., *Org. Sytheses,* (1954), Coll. Vol. 3, 328–329). The resulting 4-N-methylaminopentanoic acid methylammonium salt was then cyclized to the corresponding lactam by filtration of the product mixture and distillation of the filtrate to remove water and methylamine. N-alkyl lactams have also been produced by the direct hydrogenation of an aqueous mixture containing 2-methylglutaronitrile, a primary alkylamine, and a hydrogenation catalyst, the process yielding a mixture of 1,3- and 1,5-dialkylpiperidone-2 (U.S. Pat. No. 5,449,780). N-Substituted 2-pyrrolidinones have been prepared by the reaction of γ-valerolactone with an alkyl amine at 110–130° C., then heating the resulting mixture to 250–270° C. while distilling off water (F. B. Zienty and G. W. Steahly, *J. Am. Chem. Soc.,* (1947), vol. 69, 715–716).

The above processes for the production of lactams or N-alkyllactams suffer from one or more of the following disadvantages: the use of temperatures in excess of 250° C. to obtain high yields of lactams when using water as a solvent, the removal of water from the reaction mixture to drive the equilibrium toward lactam formation, the adjustment of the pH of the reaction mixture to an acidic value to favor lactam formation, or the use of an organic solvent in which the starting material is sparingly soluble. Many of these processes generate undesirable waste streams, or mixtures of products which are not easily separated. A significant advance would be a process for the conversion of an aliphatic α,ω-dinitrile to the corresponding lactam or N-methyllactam in aqueous solution, in high yield with high regioselectivity, with little byproduct or waste stream production, and with a facile method of product recovery.

SUMMARY OF THE INVENTION

A process for the preparation of five-membered ring lactams or six-membered ring lactams from aliphatic α,ω-dinitriles, having the steps:

(a) contacting an aliphatic α,ω-dinitrile in an aqueous reaction mixture with an enzyme catalyst characterized by either
 (1) an aliphatic nitrilase activity, or
 (2) a combination of nitrile hydratase and amidase activities, whereby the aliphatic α,ω-dinitrile is converted to an ω-nitrilecarboxylic acid ammonium salt;

(b) contacting the aqueous product mixture resulting from step (a) with hydrogen and a hydrogenation catalyst, whereby the (ω-nitrile carboxylic acid ammonium salt is converted directly to the corresponding lactam without isolation of the intermediate ω-nitrilecarboxylic acid, ω-nitrilecarboxylic acid, ammonium salt, ω-aminocarboxylic acid, or ω-aminocarboxylic acid ammonium salt; and (c) recovering the lactam from the aqueous product mixture resulting from step (b).

Prior to step (b), ammonium hydroxide, ammonia gas, or methylamine may be added to the aqueous product mixture of step (a). This addition may be from 0 to 4 molar equivalents relative to the amount of ω-nitrilecarboxylic acid ammonium salt present.

A further embodiment of the invention is a method for treating a whole cell catalyst to select for a regioselective nitrilase activity or nitrile hydratase activity capable of catalyzing the conversion of aliphatic α,ω-dinitriles to the corresponding ω-cyanocarboxylic acid ammonium salt. The whole cell catalyst to be treated is characterized by two types of activities: (1) a desirable regioselective nitrilase activity or regioselective nitrile hydratase activity and (2) an undesirable non-regioselective nitrilase or nitrile hydratase activity. Treatment of the cell involves heating the whole cell catalyst to a temperature of about 35° C. to 70° C. for between 10 and 120 minutes wherein the undesirable non-regioselective nitrilase activity or nitrile hydratase activity is destroyed and the desirable regioselective nitrilase or nitrile hydratase activity is preserved.

Further embodiments of the invention use enzyme catalysts in the form of whole microbial cells, permeabilized microbial cells, one or more cell components of a microbial cell extract, and partially purified enzyme(s), or purified enzyme(s). These enzyme catalysts can be immobilized on a support. Microorganisms which are characterized by an aliphatic nitrilase activity and useful in the process are *Acidovorax facilis* 72-PF-15 (ATCC 55747), *Acidovorax facilis* 72-PF-17 (ATCC 55745), and *Acidovorax facilis* 72W (ACC 55746). A microorganism characterized by a combination of nitrile hydratase and amidase activities and useful in the process is *Comomonas testosteroni* 5-MGAM-4D (ATCC 55744).

BRIEF DESCRIPTION OF THE BIOLOGICAL DEPOSITS

Applicants have made the following biological deposits under the terms of the Budapest Treaty:

| Depositor Identification Reference | Int'l. Depository Designation | Date of Deposit |
|---|---|---|
| *Comomonas testosteroni* 5-MGAM-4D | ATCC 55744 | 8 March 1996 |
| *Acidovorax facilis* 72-PF-17 | ATCC 55745 | 8 March 1996 |
| *Acidovorax facilis* 72W | ATCC 55746 | 8 March 1996 |
| *Acidovorax facilis* 72-PF-15 | ATCC 55747 | 8 March 1996 |

As used herein, "ATCC" refers to the American Type Culture Collection international depository located as 10801 University Blvd., Manassas, Va. 20110-2209, U.S.A. The "ATCC No." is the accession number to cultures on deposit with the ATCC.

DETAILED DESCRIPTION OF THE INVENTION

A process to prepare lactams from aliphatic α,ω-dinitriles in high yields has been developed which utilizes a combination of enzymatic and chemical reactions. In cases where the α,ω-dinitrile is unsymmetrically substituted, high regioselectivity to one of two possible lactam products (Scheme 1) is seen.

Scheme 1.

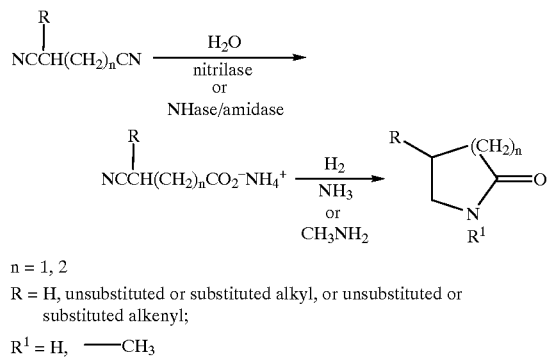

n = 1, 2
R = H, unsubstituted or substituted alkyl, or unsubstituted or substituted alkenyl;
$R^1$ = H, ——$CH_3$ The products of the present invention are useful as precursors for polymers, solvents, and chemicals of high value in the agricultural and pharmaceutical industries. The process uses temperatures less than 250° C. to obtain a high yield of lactam when using water as a solvent. Relative to previously known chemical lactam processes, the claimed invention generates little waste and permits a facile approach to product recovery.

In the application, unless specifically stated otherwise, the following abbreviations and definitions apply:

"Enzyme catalyst" refers to a catalyst which is characterized by either a nitrilase activity or a combination of a nitrile hydratase activity and an amidase activity. The catalyst may be in the form of a whole microbial cell, permeabilized microbial cell(s), one or more cell component of a microbial cell extract, partially purified enzyme(s), or purified enzyme(s).

"Hydrogenation catalyst" refers to a material that accelerates hydrogenation without itself being consumed or undergoing a chemical change.

"Aqueous product mixture" is used to refer to an aqueous mixture containing a product resulting from the corresponding process step.

A. Conversion of an aliphatic α,ω-dinitrile to the corresponding ω-nitrilecarboxylic acid ammonium salt in high yield and with high regioselectivity.

The first step of this process is the conversion of an aliphatic α,ω-dinitrile to the corresponding ω-nitrilecarboxylic acid ammonium salt, using an enzyme catalyst. The enzyme catalyst has either a nitrilase activity, where the nitrilase converts the α,ω-dinitrile directly to a corresponding ω-nitrilecarboxylic acid ammonium salt (eqn. 1), or a combination of two enzyme activities, nitrile hydratase (NHase) and amidase, where the aliphatic α,ω-dinitrile is initially converted to a ω-nitrilealkylamide by the nitrile hydratase, and then the ω-nitrilealkylamide is subsequently converted by the amidase to the corresponding ω-nitrilecarboxylic acid ammonium salt (eqn. 2):

(1)

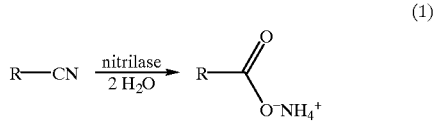

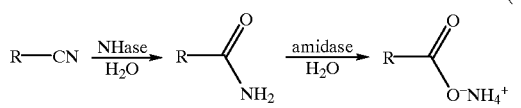

$$\text{R—CN} \xrightarrow[H_2O]{NHase} \text{R}-\underset{NH_2}{\overset{O}{\diagdown\!\!\!\diagup}} \xrightarrow[H_2O]{amidase} \text{R}-\underset{O^-NH_4^+}{\overset{O}{\diagdown\!\!\!\diagup}} \quad (2)$$

A novel microbe *Acidovorax facilis* 72W (ATCC 55746) has been isolated from soil samples which had been exposed to aliphatic nitriles or dinitriles, and which could utilize 2-ethylsuccinonitrile as a nitrogen source. When used as a microbial whole-cell catalyst for the hydrolysis of unsymmetrically substituted α-alkyl-α,ω-dinitriles such as 2-methylglutaronitrile (2-MGN) or 2-ethyl-succinonitrile (2-ESN), a mixture of products is obtained. Over the course of the hydrolysis reactions, the corresponding dicarboxylic acid monoamides and dicarboxylic acids are produced in addition to the desired ω-nitrilecarboxylic acid. It was discovered that heating a suspension of *Acidovorax facilis* 72W (ATCC 55746) in a suitable buffer at 50° C. for a short period of time deactivates an undesirable nitrile hydratase activity of the whole-cell catalyst which catalyzed the production of the undesirable dicarboxylic acid monoamides (and which were further converted by an amidase to the corresponding dicarboxylic acid). In this manner, a whole-cell catalyst is prepared which contains a nitrilase activity which converts an ω-alkyl-α,ω-dinitrile to only the ω-nitrilecarboxylic acid ammonium salt resulting from hydrolysis of the ω-nitrile group.

Heat-treatment of suspensions of *Acidovorax facilis* 72W (ATCC 55746) at 50° C. for one hour produces a microbial whole-cell catalyst which hydrolyzes 2-methylglutaronitrile (2-MGN) to 4-cyanopentanoic acid (4-CPA) ammonium salt, 2-methyleneglutaronitrile (2-MEGN) to 4-cyano-4-pentenoic acid (4-CPEA) ammonium salt, or 2-ethylsuccinonitrile (2-ESN) to 3-cyanopentanoic acid (3-CPA) ammonium salt with extremely high regioselectivity, such that at complete conversion of the dinitrile, at least a 98% yield of the ω-nitrilecarboxylic acid ammonium salt is produced by hydrolysis of the ω-nitrile group (Table 1):

TABLE 1

| α,ω-dinitrile | w-nitrile/acid ammonium salt | concentration (M) | yield (%) |
|---|---|---|---|
| 2-MGN | 4-CPA(NH$_4^+$) | 0.10 | 99.3 |
| 2-MGN | 4-CPA(NH$_4^+$) | 0.40 | 99.4 |
| 2-MGN | 4-CPA(NH$_4^+$) | 1.00 | 98.7 |
| 2-MGN | 4-CPA(NH$_4^+$) | 1.85 | 100 |
| 2-MGN | 4-CPA(NH$_4^+$) | 2.00 | 100 |
| 2-MEGN | 4-CPEA(NH$_4^+$) | 1.25 | 100 |
| 2-MEGN | 4-CPEA(NH$_4^+$) | 2.00 | 100 |
| 2-ESN | 3-CPA(NH$_4^+$) | 0.10 | 100 |
| 2-ESN | 3-CPA(NH$_4^+$) | 0.40 | 100 |
| 2-ESN | 3-CPA(NH$_4^+$) | 1.00 | 100 |
| 2-ESN | 3-CPA(NH$_4^+$) | 1.25 | 100 |

There are currently no non-enzymatic methods for the selective hydrolysis of only one nitrile group of an aliphatic dinitrile to either an amide group or a carboxylic acid group at complete conversion of the dinitrile. If such a reaction is run to incomplete conversion (<20% conversion) in order to obtain a high selectivity to a monoamide or monoacid hydrolysis product, a separation step is then required to isolate the product from unreacted dinitrile, and for recycle of dinitrile into a subsequent reaction. Non-enzymatic hydrolysis reactions also typically involve heating solutions of the nitrile or dinitrile at elevated temperatures, often times in the presence of strong acid or base, while the enzyme-catalyzed reaction described above are carried out at ambient temperature in aqueous solution and at neutral pH with no added acid or base.

Two mutants of the *Acidovorax facilis* 72W (ATCC 55746) strain have been prepared which produce only very low levels of the undesirable nitrile hydratase activity responsible for the formation of undesirable byproducts. These mutant strains, *Acidovorax facilis* 72-PF-15 (ATCC 55747) and *Acidovorax facilis* 72-PF-17 (ATCC 55745), do not require heat-treatment of the cells prior to use as catalyst for the hydrolysis of an aliphatic α,ω-dinitrile to the corresponding ammonium salt of a ω-nitrilecarboxylic acid. A comparison of the yields of 4-CPA and 2-methylglutaric acid (2-MGA) produced by the hydrolysis of 2-MGN using untreated and heat-treated *Acidovorax facilis* 72W (ATCC 55746), and the untreated *Acidovorax facilis* 72-PF-15 (ATCC 55747) mutant strain are shown in Table 2:

TABLE 2

| catalyst | [2-MGN] (M) | 4-CPA (% yield) | 2-MGA (% yield) |
|---|---|---|---|
| *A. facilis* 72W, untreated | 0.10 | 62.7 | 34.6 |
| *A. facilis* 72W, heat-treated | 0.10 | 99.3 | 0.7 |
| *A. facilis* 72-PF-15, untreated | 0.10 | 96.8 | 3.6 |
| *A. facilis* 72W, heat-treated | 0.40 | 99.4 | 0.6 |
| *A. facilis* 72-PF-15, untreated | 0.40 | 98.8 | 1.2 |
| *A. facilis* 72W, heat-treated | 1.00 | 98.7 | 1.3 |
| *A. facilis* 72-PF-15, untreated | 1.00 | 99.2 | 0.8 |

When heat-treated *Acidovorax facilis* 72W (ATCC 55746) is used as a catalyst for the hydrolysis of aqueous solutions of the unsubstituted aliphatic α,ω-dinitriles succinonitrile (SCN, 1.25 M) or glutaronitrile (GLN, 1.5 M), the corresponding ω-nitrilecarboxylic acid ammonium salts 3-cyanopropionic acid (3-CPRA) and 4-cyanobutyric acid (4-CBA) are produced in yields of 99.7% and 92.3%, respectively, and the corresponding dicarboxylic acids are the only observed byproducts. When this same catalyst is used to convert adiponitrile (ADN) to 5-cyanopentanoic acid (5-CPA) ammonium salt, adipic acid (ADA) diammonium salt is the major product (>50% yield). Neither *Acidovorax facilis* 72W (ATCC 55746) nor *Acidovorax facilis* 72-PF-15 (ATCC 55747) are suitable as catalyst for the preparation of 5-CPA ammonium salt in high yield.

More than 30 different microbial cultures isolated from soil samples which had been exposed to aliphatic nitriles or dinitriles, and which could grow on various nitriles or amides as nitrogen source, were screened for high selectivity for 5-CPA production. A second novel microbe, *Comamonas testosteroni* 5-MGAM-4D (ATCC 55744), was isolated (using 2-methylglutaramide as nitrogen source) which contained several nitrile hydratase and amidase activities. When used as a whole cell catalyst for the hydrolysis of ADN, the resulting product mixture is composed primarily of ADA diammonium salt, adipamide (ADAM) and adipamic acid (ADMA), with only a minor yield of 5-CPA ammonium salt observed. It was again found that heating the microbe at 50° C. for a short period of time deactivated an undesirable nitrile hydratase activity to a great extent, leaving the microbial catalyst with a nitrile hydratase activity which converts ADN to 5-cyanovaleramide, and an amidase which converts 5-cyanovaleramide to 5-CPA ammonium salt. Heat-treatment of *Comamonas testosteroni* 5-MGAM-4D at 50° C. for one hour results in a microbial cell catalyst which produces 5-CPA in yields as high as 97% at complete conversion of ADN.

The ability to eliminate unwanted nitrile hydratase by heat treatment, while at the same time leaving a relatively heat-stable nitrilase activity or nitrile hydratase activity for the conversion of dinitriles to the cyano acids was not previously known and could not have been predicted because the temperature stability of the nitrilase or nitrile hydratase enzyme was unknown. It is expected that heat treatment at temperatures between 35° C. and 70° C. for between 10 and 120 minutes will produce the described useful effect.

B. Preparation of five- or six-membered ring lactams.

A method has been discovered for the preparation of five-membered ring or six-membered ring lactams in high yields by the direct hydrogenation of the ω-nitrilecarboxylic acid ammonium salt product mixture produced by the enzyme-catalyzed hydrolysis of aliphatic α,ω-dinitriles in aqueous solution. This method does not require the isolation of the ω-nitrilecarboxylic acid ammonium salt from the product mixture of the hydrolysis reaction prior to the hydrogenation step, nor does it require the conversion of the ω-nitrilecarboxylic acid ammonium salt to the free acid (e.g., conversion of 4-CPA ammonium salt to 4-CPA) prior to hydrogenation, or isolation of the resulting ω-aminocarboxylic acid ammonium salt from the hydrogenation product mixture and conversion of the ammonium salt to the free carboxylic acid prior to cyclization.

After producing an aqueous product mixture containing the ammonium salt of a ω-nitrilecarboxylic acid from an aliphatic α,ω-dinitrile by using an enzyme catalyst (eqn. 3), removal of the enzyme catalyst and reaction of the resulting aqueous solution with hydrogen and a stoichiometric excess of added ammonia (as ammonium hydroxide) in the presence of a suitable hydrogenation catalyst was expected to produce an aqueous solution containing an aliphatic ω-aminocarboxylic acid ammonium salt (eqn. 4):

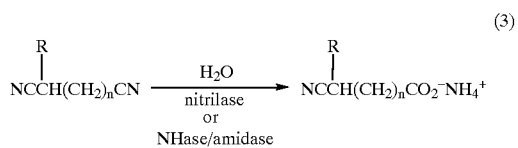

(3)

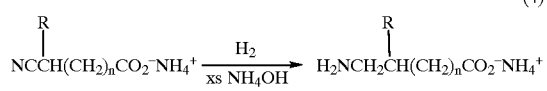

(4)

The use of an excess of ammonia during the hydrogenation of a nitrile to the corresponding amine is necessary to limit reductive alkylation of an amine intermediate (produced during the hydrogenation of the nitrile group to an amine) by the product ω-aminocarboxylic acid, which results in dimer formation and yield loss. This technique is well-documented (De Bellefon et al., *Catal. Rev. Sci. Eng.*, (1994), vol. 36, 459–506) and is commonly practiced by those skilled in the art of hydrogenation of nitriles.

Based on the prior art, it was expected that the ω-aminocarboxylic acid ammonium salt produced by the hydrogenation of a ω-nitrilecarboxylic acid ammonium salt would have to be converted to the free acid and isolated (eqn. 5) before a thermally-induced cyclization reaction to produce the desired lactam could be performed (eqn. 6). According to Mares et al. (supra), 6-aminocaproic acid (6-ACA) (eqn. 6, n=3, R=H) and caprolactam exist as a reversible equilibrium mixture at concentrations of less than 1.0 mol/kg (ca. 1.0 M) in water and the concentration of caprolactam increases with increasing temperature. At a total concentration of 6-ACA and caprolactam of 0.85 mol/kg (ca. 0.85 M), the percentage of caprolactam was reported by Mares et al. to increase from 38.7% at 180° C. to 92.2% at 250° C.

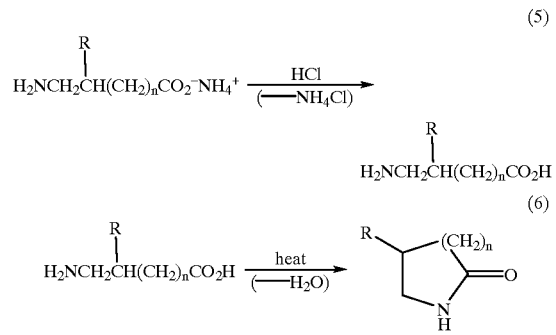

In the present case, where an excess of added ammonia (as ammonium hydroxide) is present and the pH of the reaction mixture is between pH 9 and pH 10, it was not expected that the ammonium salt of 6-ACA would cyclize to produce significant amounts of caprolactam at hydrogenation temperatures of less than 200° C. The pKa's of the carboxylic acid group and the protonated amine group of 6-aminocaproic acid are 4.373 and 10.804, respectively (Lange's Handbook of Chemistry, J. A. Dean, ed., 14th edn., (1992), McGraw-Hill, NY, p. 8.22 (as 6-aminohexanoic acid)), and the pKa of $NH_4^+$ is 9.25. At a reaction mixture pH of between 9 and 10, it can be calculated that at least 99.997% of the 6-ACA exists in solution as the ammonium salt of the carboxylic acid, and additionally, approximately half of the amine groups of the 6-aminocaproic acid ammonium salt are also protonated. Therefore, it was not expected that significant amounts of the 6-ACA ammonium salt would cyclize to produce caprolactam under the hydrogenation conditions of the present invention, where displacement of a hydroxyl anion ($^-OH$) from the cyclic reaction intermediate is not possible (eqn. 7):

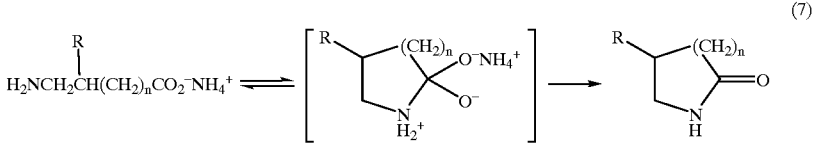

(7)

When hydrogenations of aqueous solutions of 5-CPA ammonium salt (prepared by enzymatic hydrolysis of ADN) are performed in the presence of from 0 M to 2.0 M $NH_4OH$ at temperatures of from 70° C. to 160° C., complete conversion of 5-CPA to 6-ACA ammonium salt was observed with little byproduct formation, and, as predicted, less than 3% yields of caprolactam (the resulting seven-membered ring lactam) are obtained (Table 3):

TABLE 3

| Temp. (° C.) | 5-CPA ammonium salt (M) | [NH₄OH] (M) | time (h) | 5-CPA conv. (%) | caprolactam (%) |
|---|---|---|---|---|---|
| 70  | 1.0 | 0   | 2 | 100 | 0.7 |
| 70  | 1.0 | 1.0 | 2 | 100 | 0.7 |
| 70  | 1.0 | 1.5 | 2 | 94  | 0.8 |
| 70  | 1.0 | 2.0 | 2 | 84  | 0.9 |
| 120 | 1.0 | 0   | 2 | 99  | 0.9 |
| 120 | 1.0 | 1.0 | 2 | 100 | 0.9 |
| 120 | 1.0 | 1.5 | 2 | 97  | 1.0 |
| 120 | 1.0 | 2.0 | 2 | 97  | 1.1 |
| 160 | 1.0 | 0   | 2 | 97  | 2.5 |
| 160 | 1.0 | 1.0 | 2 | 84  | 2.3 |
| 160 | 1.0 | 1.5 | 2 | 97  | 3.0 |
| 160 | 1.0 | 2.0 | 2 | 95  | 2.7 |

Yields of caprolactam of less than 3% are also obtained when aqueous solutions prepared by mixing authentic 6-ACA and ammonium hydroxide are treated under the same hydrogenation reaction conditions as for hydrogenation of the ammonium salt of 5-CPA prepared by enzymatic hydrolysis of ADN. The cyclization of the ammonium salt of 6-ACA in aqueous solutions prepared by the hydrogenation of 5-CPA ammonium salt at 70° C. was attempted at temperatures greater than 200° C. by first removing the hydrogenation catalyst, then heating the ca. 1.0 M 6-ACA ammonium salt product mixtures at 280° C. for 2 h. Yields of caprolactam of less than 18% were produced (Table 4). These results demonstrate that only very low yields of caprolactam are obtained by the direct hydrogenation of aqueous solutions of 5-CPA ammonium salt in the presence of excess ammonia. This was expected in light of the predicted inability of the 6-ACA ammonium salt to undergo cyclization, particularly in the presence of excess ammonium hydroxide.

TABLE 4

| Temp. (° C.) | 6-ACA ammomium salt (M) | [NH₄OH] (M) | time (h) | caprolactam (%) |
|---|---|---|---|---|
| 280 | 1.0 | 0   | 2 | 17.8 |
| 280 | 1.0 | 1.0 | 2 | 17.2 |
| 280 | 1.0 | 1.5 | 2 | 11.0 |
| 280 | 1.0 | 2.0 | 2 | 9.0  |
| 280 | 1.0 | 2.5 | 2 | 3.1  |

It was also expected that when aqueous mixtures of 3-cyanopentanoic acid (3-CPA) ammonium salt (prepared by enzymatic hydrolysis of 2-ethylsuccinonitrile (2-ESN)) or 4-cyanovaleric acid (4-CPA) ammonium salt (prepared by enzymatic hydrolysis of 2-methylglutaronitrile (2-MGN)) were hydrogenated at from 70° C. to 160° C. in the presence of excess ammonia, the corresponding ω-aminocarboxylic acid ammonium salts would be produced, and that these salts would have to be isolated as the free acids before the cyclization reaction to the corresponding lactam could be performed (as was the case for 5-CPA ammonium salt). Although the pKa's of the carboxylic acid and the protonated amine functionalities of the product 4-amino-3-ethylbutyric acid or 5-amino-4-methylpentanoic acid have not been reported, it is reasonable to assume that these pKas are similar to those of the 6-ACA isomer.

Unexpectedly, hydrogenation of aqueous solutions of 3-CPA ammonium salt (produced by enzymatic hydrolysis of 2-ESN) in the presence of Raney nickel and excess ammonia at pH 9–10 and at temperatures of from 70° C. to 180° C. for 2 h produce the corresponding lactam 4-ethylpyrrolidin-2-one (4-EPRD) directly, and at yields of up to 91% (Table 5). The yield of 4-EPRD also increases with increasing concentration of added ammonium hydroxide (added in addition to the ammonium ion concentration already present as the ammonium salt of the carboxylic acid), which indicates the desirability of performing the hydrogenation of aqueous solutions of the ammonium salts of the mononitrile acids in the presence of added ammonia in order to limit well-known reductive alkylation reactions which produce dimer and polymer (Table 6).

TABLE 5

| Temp. (° C.) | 3-CPA ammonium salt (M) | [NH₄OH] (M) | wt. % Raney Ni | time (h) | 3-CPA (% conv.) | 4-EPRD (% yield) |
|---|---|---|---|---|---|---|
| 70  | 1.0 | 2.0 | 5  | 2 | 7   | 1.5  |
| 120 | 1.0 | 2.0 | 5  | 2 | 55  | 22.7 |
| 140 | 1.0 | 2.0 | 5  | 2 | 71  | 55.4 |
| 140 | 1.0 | 2.0 | 10 | 2 | 100 | 89.9 |
| 160 | 1.0 | 2.0 | 5  | 2 | 100 | 90.1 |
| 160 | 1.0 | 2.0 | 10 | 2 | 100 | 91.3 |
| 180 | 1.0 | 2.0 | 5  | 2 | 100 | 86.1 |
| 180 | 1.0 | 2.0 | 10 | 2 | 100 | 90.0 |

TABLE 6

| Temp. (° C.) | 3-CPA ammonium salt (M) | [NH₄OH] (M) | wt. % Raney Ni | time (h) | 3-CPA (% conv.) | 4-EPRD (% yield) |
|---|---|---|---|---|---|---|
| 160 | 1.0 | 0   | 5 | 2 | 99  | 80.1 |
| 160 | 1.0 | 1.0 | 5 | 2 | 99  | 87.6 |
| 160 | 1.0 | 2.0 | 5 | 2 | 100 | 90.1 |
| 160 | 1.0 | 3.0 | 5 | 2 | 100 | 85.4 |
| 180 | 1.0 | 0   | 5 | 2 | 100 | 75.1 |
| 180 | 1.0 | 1.0 | 5 | 2 | 100 | 85.8 |
| 180 | 1.0 | 2.0 | 5 | 2 | 100 | 88.5 |
| 180 | 1.0 | 3.0 | 5 | 2 | 100 | 90.0 |

The hydrogenation of aqueous solutions of 4-CPA ammonium salt (produced by enzymatic hydrolysis of 2-MGN) in the presence of Raney nickel and excess ammonia at pH 9–10 and at 160° C. for 2 h produces the corresponding lactam 5-methyl-2-piperidone (5-MPPD) directly, and at yields as high as 96% (Table 7):

TABLE 7

| Temp. (° C.) | 4-CPA ammonium salt (M) | [NH₄OH] (M) | wt. % Raney Ni | time (h) | 4-CPA (% conv.) | 5-MPPD (% yield) |
|---|---|---|---|---|---|---|
| 160 | 1.0 | 0   | 5 | 2 | 100 | 85.6 |
| 160 | 1.0 | 2.0 | 5 | 3 | 100 | 96.4 |
| 180 | 1.0 | 2.0 | 5 | 2 | 100 | 91.4 |
| 180 | 1.0 | 3.0 | 5 | 2 | 100 | 89.5 |

Hydrogenation of aqueous solutions of the ammonium salts of 3-cyano-propionic acid (3-CPRA) or 4-cyanobutyric acid (4-CBA) (produced by enzymatic hydrolysis of the corresponding α,ω-dinitriles) produce the corresponding lactams 2-pyrrolidinone and 2-piperidone in 91.0% yield and 93.5% yield, respectively. Hydrogenation of aqueous solutions of 4-cyano-4-pentenoic acid (4-CPEA) ammonium salt (produced by enzymatic hydrolysis of 2-methyleneglutaronitrile) result in hydrogenation of both the nitrile and carbon-carbon double bond to produce 5-methyl-2-piperidone in up to 85% yield.

By adding an excess of ammonia (as ammonium hydroxide) to the hydrogenation reactions in order to limit reductive alkylation during the hydrogenation of nitriles to amines, several additional byproduct-forming reactions could also have occurred (De Bellefon et al., *Catal. Rev. Sci. Eng.*, (1994), vol. 36, 459–506). It is well-known to those skilled in the art that a common method for the preparation of an amide or carboxylic acid from a nitrile is to heat an aqueous mixture of the nitrile in the presence of an acid or base catalyst. Therefore, an expected competing reaction of the ammonium salt of a mononitrile carboxylic acid under the hydrogenation conditions used in the present invention would be the base-catalyzed hydrolysis of the nitrile group to produce either the dicarboxylic acid monoamide ammonium salt or the dicarboxylic acid diammonium salt. These unwanted amide/acid and dicarboxylic acid ammonium salts byproducts are produced during the hydrogenations, but in very low yields compared to the yields of lactam.

A second byproduct-forming reaction between the excess ammonia present and the product lactam could have produced an equilibrium mixture of the lactam with the expected ammonolysis product, an ω-aminocarboxamide. The high yields of the five-membered and six-membered ring lactams attained under the present reaction conditions suggest that the ammonolysis (or base-catalyzed hydrolysis) of the product lactams is not significant.

In addition to producing lactams from aliphatic α,ω-dinitriles, N-methyl-lactams are prepared by the substitution of methylamine for ammonia in the hydrogenation of aqueous solutions of the ammonium salts of 4-CPA or 3-CPA. Addition of from one to four equivalents of methylamine (pKa 10.62 for the protonated amine) to an aqueous solution of 4-CPA containing one equivalent of ammonium ion (pKa 9.25) was expected to produce a significant amount of free ammonia (due to the relative differences in pKa's of protonated methylamine and ammonium ions in water). This free ammonia could then compete with unprotonated methylamine for reaction with the intermediate imine produced during the hydrogenation of the nitrile group, leading to the production of a mixture of the ammonium salts of 5-amino-4-methylpentanoic acid and 5-N-methylamino-4-methylpentanoic acid, respectively, which in turn cyclize to produce 5-MPPD and 1,5-dimethyl-2-piperidone (1,5-DMPD), respectively.

The relative yields of 5-MPPD and 1,5-DMPD produced by hydrogenation of 1.0 M aqueous solutions of the ammonium salt of 4-CPA are found to be dependent on the choice of catalyst. Raney nickel and ruthenium on alumina each produce 5-MPPD as the major lactam product, even in the presence of 3.0 M methylamine, while 1,5-DMPD is the major product when using 5% Pd/C or 4.5% Pd/0.5% Pt/C as catalyst at the same methylamine concentration. When using 5% Pd/C as catalyst, the yield of 1,5-DMPD increases with increasing concentration of methylamine (Table 8).

The substitution of 2.0 M methylamine for ammonia in the hydrogenation of an aqueous solutions of 1.0 M 3-CPA ammonium salt at 140° C. and using a Pd/C catalyst produces 4-ethyl-1-methylpyrrolidin-2-one (4-EMPRD) and 4-EPRD in 69.8% and 20.4% yields, respectively, at 96% conversion.

TABLE 8

| Temp. (° C.) | 4-CPA(NH$_4^+$) (M) | CH$_3$NH$_2$ (M) | catalyst | time (h) | 4-CPA (% conv) | 1,5-DMPD (% yield) | 5-MPPD (% yield) |
|---|---|---|---|---|---|---|---|
| 160 | 1.0 | 3.0 | Ra-Ni | 2 | 100 | 19.2 | 68.5 |
| 160 | 1.0 | 3.0 | RuAl$_2$O$_3$ | 2 | 100 | 19.0 | 63.5 |
| 140 | 1.0 | 3.0 | Pd/C | 2 | 99 | 83.4 | 0 |
| 160 | 1.0 | 1.0 | Pd/C | 2 | 100 | 53.5 | 0 |
| 160 | 1.0 | 1.25 | Pd/C | 2 | 100 | 68.3 | 0 |
| 160 | 1.0 | 1.5 | Pd/C | 2 | 100 | 76.4 | 0 |
| 160 | 1.0 | 2.0 | Pd/C | 2 | 100 | 81.5 | 0 |
| 160 | 1.0 | 3.0 | Pd/C | 2 | 100 | 81.7 | 7.8 |
| 160 | 1.0 | 4.0 | Pd/C | 2 | 100 | 88.4 | 1.9 |
| 180 | 1.0 | 3.0 | Pd/C | 2 | 97 | 73.0 | 6.6 |
| 160 | 1.4 | 2.3 | Pd/Pt/C | 2 | 99 | 94.0 | 3.1 |

DESCRIPTION OF THE PREFERRED EMBODIMENTS

Methods and Materials

Microbial Catalysts for the Preparation of ω-Nitrilecarboxylic Acids

Two microorganisms have been isolated for use as a microbial catalyst for the conversion of aliphatic α,ω-dinitriles to the corresponding ω-nitrilecarboxylic acids: *Acidovorax facilis* 72W (ATCC 55746) and *Comamonas testosteroni* 5-MGAM-4D (ATCC 55744).

*Acidovorax facilis* 72W (ATCC 55746) was isolated from soil collected in Orange, Tex. Standard enrichment procedures were used with the following medium (E2 Basal Medium, pH 7.2):

| E2 Basal Medium | g/L |
|---|---|
| KH$_2$PO$_4$ | 1.4 |
| NaH$_2$PO$_4$ | 0.69 |
| Sodium citrate | 0.1 |
| CaCl$_2$ · 2H$_2$O | 0.025 |
| KCl | 0.5 |
| NaCl | 1.0 |
| MgSO$_4$ · 7H$_2$O | 0.5 |
| FeSO$_4$ · 7H$_2$O | 0.05 |
| CoCl$_2$ · 6H$_2$O | 0.01 |
| MnCl$_2$ · 4H$_2$O | 0.001 |
| ZnCl$_2$ | 0.0005 |
| NaMoO$_4$ · 2H$_2$O | 0.0025 |
| NiCl$_2$ · 6H$_2$O | 0.01 |
| CuSO$_4$ · 2H$_2$O | 0.005 |
| Biotin | 0.0002 |
| Folic Acid | 0.0002 |
| Pyridoxine · HCl | 0.001 |
| Riboflavine | 0.0005 |
| Thiamine · HCl | 0.00005 |
| Nicotinic Acid | 0.0005 |
| Pantothenic Acid | 0.0005 |
| Vitamin B$_{12}$ | 0.00001 |
| p-Aminobenzoic Acid | 0.0005 |

The following supplementations were made to the E2 basal medium for the enrichments described above:

| Strain | Enrichment Nitrogen Source | Other Supplements |
|---|---|---|
| A. facilis 72W | 0.2 % (v/v) ethylsuccinonitrile | 0.3% (v/v) glycerol |

Strains were originally selected based on growth and ammonia production on the enrichment nitrile. Isolates were purified by repeated passing on Bacto® Brain Heart Infusion Agar (Difco, Detroit, Mich.) followed by screening for ammonia production from the enrichment nitrile. Purified strains were identified based on their carbon source utilization profile on a Biolog® test system (Hayward, Calif., USA) using Gram negative test plates.

For testing nitrile hydrolysis activity, E2 basal medium with 10 g/L glucose was used to grow A. facilis 72W. The medium was supplemented with 25 mM (±)-2-methylglutaronitrile. A 10 mL volume of supplemented E2 medium was inoculated with 0.1 mL of frozen stock culture. Following overnight growth at room temperature (22–25° C.) on a shaker at 250 rpm, the 10 mL inoculum was added to 990 mL of fresh medium in a 2 L flask. The cells were grown overnight at room temperature with stirring at a rate high enough to cause bubble formation in the medium. Cells were harvested by centrifugation, washed once with 50 mM phosphate buffer(pH 7.2)/15% glycerol and the concentrated cell paste was immediately frozen on dry ice and stored at −65° C. Adiponitrile, 10 mM, was also used in the 1 liter fermentations. Fermentations were stopped after 16–20 hours of growth. The cell suspension was chilled to 4° C., harvested by centrifugation and frozen at −60° C. following one wash with 15% glycerol in 0.05 M phosphate buffer, pH 7.2. Thawed cell pastes were used for testing nitrile hydrolysis activity. The desired property of the microorganism is a nitrile hydrolyzing activity capable of regiospecific attack of a dinitrile compound in the absence of interfering amidase activity. Microorganisms tend to undergo mutation. Some mutations may be favorable to the desired nitrile conversion. Thus, even mutants of the native strain may be used to carry out the process of the instant invention.

Standard enrichment procedures were also used for Comamonas testosteroni 5-MGAM-4D with E2 Basal Medium, pH 7.2 modified by having vitamins at one tenth the concentration in the standard basal medium described above. The following supplementations were made to the modified E2 basal medium for the enrichments:

| Strain | Enrichment Nitrogen Source | Other Supplements |
|---|---|---|
| C. testosteroni 5-MGAM-4D | 2-Methylglutaramide (MGAM; 1.0% w/v) | glycerol (0.6%) |

Strains were originally selected based on growth on the enrichment nitrile-amide. Isolates were purified by repeated passing on agar plates using the above medium. Purified strains were identified based on their carbon source utilization profile on a Biolog® test system (Hayward, Calif., USA) using Gram negative test plates.

For testing nitrile hydrolysis activity, modified E2 basal medium with 6.0 g/L of either glucose or glycerol was used to grow cell material. The medium was supplemented with 1.0% MGAM. A 250 mL unbaffled shake flask containing 50 mL of supplemented E2 medium was inoculated with 0.2 mL of frozen stock culture and grown for 72 h at 30° C. on a shaker at 200 rpm. The cells were harvested by centrifugation and washed with 10 mL of 20 mM KH2PO4, pH 7.0. The cells were screened in 10 mL reactions containing 20 mM KH2PO4, pH 7.0 and 0.1 M of either methylglutaronitrile or methylglutaramide for regiospecific hydrolysis using HPLC. The desired property of the microorganism is a nitrile hydrolyzing activity capable of regiospecific attack of a dinitrile compound in the absence of interfering amidase activity. Microorganisms tend to undergo mutation. Some mutations may be favorable to the desired nitrile conversion. Thus, even mutants of the native strain may be used to carry out the process of the instant invention.

The present invention is not limited to the particular organisms mentioned above, but includes the use of variants and mutants thereof that retain the desired property. Such variants and mutants can be produced from parent strains by various known means such as x-ray radiation, UV-radiation, and chemical mutagens.

To produce biocatalyst for process demonstration (Examples 1–26), the following media were used.

| Strain | Medium |
|---|---|
| 72-PF-15 | Lauria-Bertani Medium(Bacto ® tryptone, 10 g/L + Bacto ® yeast extract, 5 g/L + NaCl, 10 g/L) + 0.5 % (w/v) sodium succinate.6H$_2$O |
| 72 W | E2 + 1 % (w/v) glucose + 0.4 % (w/v) adipamide |
| 5-MGAM-4D | E2 + 1 % (w/v) glucose + 0.2 % (w/v) propionamide |

To initiate growth, 10 mL of the appropriate medium was inoculated with 0.1 mL of frozen stock culture. Following overnight growth at 28° C. with shaking at 250 rpm, the growing cell suspension was transferred to 1 L of the same medium in a 2 L flask and growth continued at 28° C. with shaking. The 1 L growing cell suspension was then added to 9 L of the same medium in a 10 L fermentation vessel where growth continued. Nominal conditions in the fermenter were: ≧80% oxygen saturation, 25° C., pH 7.2, 300–1000 rpm. After 20–91 hours, the vessel was chilled to 8–12° C. and glycerol added to 10% final concentration. Cell material was harvested by centrifugation. The concentrated cell paste was immediately frozen on dry ice and stored at −70° C. until use. Numerous other supplementations which will serve as carbon and nitrogen sources for cell growth in E2 basal medium are known to those skilled in the art. These, as well as complex nutrient media, can be used to produce biocatalyst. The particular media described above should not be viewed as restrictive.

Selection of Mutant Strains of Acidovorax facilis 72W Deficient in NHase Activity Mutants of Acidovorax facilis 72W (ATCC 55746) with reduced capacity to produce the undesirable 2-methylglutaric acid by-product during hydrolysis of 2-MGN to 4-CPA were selected based on their inability to use 2-MGN as a carbon and energy source. Specifically, an overnight culture of strain A. facilis 72W grown on LB/succinate medium (1% (w/v) Bacto-tryptone (Difco, Detroit, Mich., USA), 0.5% (w/v) Bacto-yeast extract (Difco, 1% (w/v) NaCl, 0.5% (w/v) sodium succinate hexahydrate) was exposed to 100 μg/mL solution of N-methyl-N'-nitro-N-nitrosoguanidine, a mutagenic agent, for approximately 30 minutes. This resulted in a 99.9% reduction in viable cells in the culture. Mutagenized cells were washed free of the mutagen by centrifugation in sterile, 1 M sodium phosphate buffer, pH 7.2. Washed cells were resuspended in LB/succinate medium and grown overnight at 30° C. Cells were then washed by centrifugation in sterile, 50 mM sodium phosphate buffer, pH 7.2, and resuspended in E2 minimal medium(without glucose) containing 0.2% (v/v) 2-methylglutaronitrile, and the antibiotics cycloserine, 0.2 mg/mL and piperacillin, 40 μg/mL. Cells were incubated overnight at 30° C. and again washed in sterile, 50 mM sodium phosphate buffer, pH 7.2. Washed cells were spread on agar plates containing a non-selective medium: E2 minimal medium(without glucose) plus 0.2% (v/v) 2-methylglutaronitrile and 0.5% (w/v) sodium succinate hexahydrate, at a concentration of 40–100 colony-forming units per plate. Plates were incubated for approximately 48 h at 30° C. to allow colonies to develop. Colonies which developed were replica plated onto agar plates containing selective medium: E2 minimal medium(without glucose) plus 0.2% (v/v) 2-MGN. Plates were incubated 48 h at 30° C. to allow colonies to develop. Mutants with desirable qualities do not grow well on the selective medium. Therefore, after 48 h, replicated plates were compared and strains showing growth only on non-selective medium were saved for further testing.

In total, approximately 5,120 colonies were checked from 89 plates and 19 strains with the desirable qualities were identified. These mutant strains were further tested for growth in liquid, E2 minimal medium(without glucose) plus 0.2% (v/v) 2-MGN. Strains which showed little or no growth in this medium were screened for their ability to produce 2-methylglutaric acid during growth in liquid medium consisting of E2 minimal medium (without glucose) plus 0.2% (v/v) 2-MGN and 0.5% (w/v) sodium succinate hexahydrate. As a result of this process, two mutant strains, identified as *Acidovorax facilis* 72-PF-15 (ATCC 55747) and *Acidovorax facilis* 72-PF17 (ATCC 55745) were chosen for further development due to their greatly diminished capacity to produce 2-methylglutaric acid.

Aliphatic α,ω-Dinitrile Hydrolysis Reactions

An aqueous solution containing the ammonium salt of an aliphatic ω-nitrilecarboxylic acid is prepared by mixing the corresponding aliphatic α,ω-dinitrile with an aqueous suspension of the appropriate enzyme catalyst (as identified in part A above). Whole microbial cells can be used as catalyst without any pretreatment. Alternatively, they can be immobilized in a polymer matrix (e.g., alginate beads or polyacrylamide gel (PAG) particles) or on an insoluble solid support (e.g., celite) to facilitate recovery and reuse of the catalyst. Methods for the immobilization of cells in a polymer matrix or on an insoluble solid support have been widely reported and are well-known to those skilled-in-the-art. The nitrilase enzyme, or nitrile hydratase and amidase enzymes, can also be isolated from the whole cells and used directly as catalyst, or the enzyme(s) can be immobilized in a polymer matrix or on an insoluble support. These methods have also been widely reported and are well-known to those skilled in the art.

Some of the aliphatic α,ω-dinitriles used as starting material in the present invention are only moderately water soluble. Their solubility is also dependent on the temperature of the solution and the salt concentration (buffer and/or ω-nitrilecarboxylic acid ammonium salt) in the aqueous phase. For example, adiponitrile was determined to have a solubility limit of ca. 0.60 M, (25° C., 20 mM phosphate buffer, pH 7) and under the same conditions, 2-methylglutaronitrile was determined to have a solubility limit of ca. 0.52 M. In this case, production of an aqueous solution of a (ω-nitrilecarboxylic acid ammonium salt at a concentration greater than the solubilty limit of the starting α,ω-dinitrile is accomplished using a reaction mixture which is initially composed of two phases: an aqueous phase containing the enzyme catalyst and dissolved α,ω-dinitrile, and an organic phase (the undissolved α,ω-dinitrile). As the reaction progresses, the dinitrile dissolves into the aqueous phase, and eventually a single phase product mixture is obtained.

The concentration of enzyme catalyst in the reaction mixture is dependent on the specific catalytic activity of the enzyme catalyst and is chosen to obtain the desired rate of reaction. The wet cell weight of the microbial cells used as catalyst in hydrolysis reactions typically ranges from 0.001 grams to 0.100 grams of wet cells per mL of total reaction volume, preferably from 0.002 grams to 0.050 grams of wet cells per mL. The specific activity of the microbial cells (IU/gram wet cell wt.) is determined by measuring the rate of conversion of a 0.10 M solution of a dinitrile substrate to the desired ω-nitrilecarboxylic acid product at 25° C., using a known weight of microbial cell catalyst. An IU (International Unit) of enzyme activity is defined as the amount of enzyme activity required to convert one micromole of substrate to product per minute.

The temperature of the hydrolysis reaction is chosen to both optimize both the reaction rate and the stability of the enzyme catalyst activity. The temperature of the reaction may range from just above the freezing point of the suspension (ca. 0° C.) to 60° C., with a preferred range of reaction temperature of from 5° C. to 35° C. The microbial cell catalyst suspension may be prepared by suspending the cells in distilled water, or in a aqueous solution of a buffer which will maintain the initial pH of the reaction between 5.0 and 10.0, preferably between 6.0 and 8.0. As the reaction proceeds, the pH of the reaction mixture may change due to the formation of an ammonium salt of the carboxylic acid from the corresponding nitrile functionality of the dinitrile. The reaction can be run to complete conversion of dinitrile with no pH control, or a suitable acid or base can be added over the course of the reaction to maintain the desired pH.

The final concentration of aliphatic o-nitrilecarboxylic acid ammonium salt in the product mixture at complete conversion of the α,ω-dinitrile may range from 0.001 M to the solubility limit of the aliphatic (ω-nitrilecarboxylic acid ammonium salt. Typically, the concentration of the ω-nitrilecarboxylic acid ammonium salt ranged from 0.10 M to 2.0 M. The product mixture of the hydrolysis reaction may be used directly in the subsequent hydrogenation reaction after recovery of the enzyme catalyst by centrifugation and/or filtration. The ω-nitrilecarboxylic acid may also be isolated from the product mixture (after removal of the catalyst) by adjusting the pH of the reaction mixture to between 2.0 and 2.5 with conc. HCl, saturation of the resulting solution with sodium chloride, and extraction of the ω-nitrilecarboxylic acid with a suitable organic solvent such as ethyl acetate, ethyl ether, or dichloromethane. The combined organic extracts are then combined, stirred with a suitable drying agent (e.g., magnesium sulfate), filtered, and the solvent removed (e.g., by rotary evaporation) to produce the desired product in high yield and in high purity (typically 98–99% pure). If desired, the product can be further purified by recrystallization or distillation.

Hydrogenation/Cyclization of ω-Nitrilecarboxylic Acid Ammonium Salts

Catalytic hydrogenation is a preferred method for preparing an aliphatic amine from an aliphatic nitrile. In the present invention, the ω-aminocarboxylic acid produced during the hydrogenation cyclizes to the corresponding five-membered or six-membered ring lactam. An aqueous solution of an ammonium salt of an ω-nitrilecarboxylic acid (prepared by centrifugation and filtration of the aqueous product mixture produced by the enzymatic hydrolysis of the corresponding aliphatic α,ω-dinitrile) is first mixed with concentrated ammonium hydroxide and water to produce a solution which contains from one to four stoichiometric equivalents of added ammonium hydroxide. The ammonium hydroxide is added to limit the reductive alkylation of the ωnitrilecarboxylic acid by the product ω-aminocarboxylic acid during the course of the hydrogenation. A two- to three-fold stoichiometric excess of the ammonium hydroxide relative to the amount of ω-nitrilecarboxylic acid present in the reaction mixture is preferred to achieve an optimum yield of the desired lactam. Optionally, ammonia gas can be substituted for the ammonium hydroxide added to the reaction mixture. The initial concentration of the ω-nitrilecarboxylic acid ammonium salt in the hydrogenation reaction mixture may range from 5 weight percent to 20 weight percent of the solution, with a preferred range of from 7.5 weight percent to 12.5 weight percent.

For the preparation of a N-methyllactam, methylamine is substituted for ammonium hydroxide or ammonia, using one to four stoichiometric equivalents relative to the amount of ω-nitrilecarboxylic acid present in the reaction mixture. A three-fold to four-fold stoichiometric excess of methylamine relative to the amount of ω-nitrilecarboxylic acid present in the reaction mixture is preferred to achieve an optimum yield of the desired N-methyllactam.

To the hydrogenation reaction mixture described above is then added a suitable hydrogenation catalyst, and the resulting mixture heated under pressure with hydrogen gas to convert the ω-nitrilecarboxylic acid ammonium salt to the corresponding five-membered or six-membered ring lactam. Hydrogenation catalysts suitable for this purpose include (but are not limited to) the various platinum metals, such as iridium, osmium, rhodium, ruthenium, platinum, and palladium; also various other transition metals such as cobalt, copper, nickel and zinc. The catalyst may be unsupported, (for example as Raney nickel or platinum oxide), or it may be supported (for example, as palladium on carbon, platinum on alumina, or nickel on kieselguhr).

The hydrogenation catalyst is used at a minimum concentration sufficient to obtain the desired reaction rate and total conversion of starting materials under the chosen reaction conditions. This concentration is easily determined by trial. The catalyst may be used in amounts of from 0.001 to 20 or more parts by weight of catalyst per 100 parts of ω-nitrilecarboxylic acid employed in the reaction. The catalyst loading in the reaction mixture is typically from 1% to 10% (weight catalyst/weight of ω-nitrilecarboxylic acid), with a 3% to 5% catalyst loading preferred. Raney nickel (e.g., Cr-promoted Raney nickel catalyst (Grace Davison Raney 2400 active metal catalyst)) is a preferred catalyst for reactions run in the presence of added ammonia to produce lactams, while 5% or 10% palladium on carbon, or 4.5% palladium/0.5% platinum on carbon are preferred for reactions run in the presence of added methylamine to produce N-methyllactams.

The hydrogenation temperature and pressure can vary widely. The temperature may generally be in the range of from 45° C. to 200° C., preferably from 70° C. to 180° C. The hydrogen pressure is generally in the range of from about atmospheric to about 100 atmospheres, preferably from 30 to 60 atmospheres. The hydrogenation is performed without any pH adjustment of the reaction mixture, which with the addition of an excess of ammonium hydroxide, ammonia, or methylamine is generally between a pH of from 9 to 12. Within this pH range, the exact value may be adjusted to obtain the desired pH by adding any compatible, non-interfering base or acid. Suitable bases include, but are not limited to, alkali metal hydroxides, carbonates, bicarbonates and phosphates, while suitable acids include, but are not limited to, hydrochloric, sulfuric, or phosphoric acid.

Lysis of the microbial cell catalysts during the hydrolysis reaction or contaminants present from the catalyst preparation could have introduced compounds into the hydrogenation reaction mixture (e.g., thiols) which could have poisoned the catalyst activity. No poisoning or deactivation of the hydrogenation catalysts was observed when comparing the hydrogenation of ω-nitrilecarboxylic acid ammonium salt mixtures produced via microbial hydrolysis with the hydrogenation of aqueous solutions of the same ω-nitrilecarboxylic acid which was isolated from the hydrolysis product mixtures and purified prior to hydrogenation.

The lactam or N-methyllactam may be readily isolated from the hydrogenation product mixture by first filtering the mixture to recover the hydrogenation catalyst, and then the product can be distilled directly from the resulting aqueous filtrate. The ammonia produced during the cyclization reaction or added to the reaction mixture can also be recovered for recycling by this distillation process, and the generation of undesirable inorganic salts as waste products is avoided. The lactams or N-methyl lactams may also be recovered by filtering the hydrogenation mixture, adjustment of the filtrate to a pH of ca. 7 with conc. HCl and saturation with sodium chloride, extraction of the lactam or N-methyllactam (batch or continuous extraction) with an organic solvent such as ethyl acetate, dichloromethane, or ethyl ether, and recovery from the organic extract by distillation or crystallization. In the accompanying examples, the isolated yields reported for this method are unoptimized, and this method was used simply to obtain purified product for analysis and confirmation of chemical identity.

In the following examples, which serve to further illustrate the invention and not to limit it, the % recovery of aliphatic α,ω-dinitriles and the % yields of the hydrolysis products formed during the microbial hydrolysis reactions were based on the initial amount of α,ω-dinitrile present in the reaction mixture (unless otherwise noted), and determined by HPLC using a refractive index detector and either a Supelcosil LC-18-DB column (25 cm×4.6 mm dia.) or a Bio-Rad HPX-87H column (30 cm×7.8 mm dia.). The yields of lactams and N-methyl-lactams produced by the hydrogenation of aqueous solutions of ω-nitrilecarboxylic acid ammonium salts were based on the initial concentration of ω-nitrilecarboxylic acid ammonium salt present in the reaction mixture (unless otherwise noted), and determined by gas chromatography using a DB-1701 capillary column (30 m×0.53 mm ID, 1 micron film thickness).

EXAMPLE 1

4-Cyanopentanoic Acid (Ammonium Salt)

First, 0.60 grams (wet cell weight) of frozen *Acidovorax facilis* 72W (ATCC 55746) cells (previously heat-treated at 50° C. for 1 h before freezing) were placed into a 15-mL polypropylene centrifuge tube and followed by addition of 12 mL of potassium phosphate buffer (20 mM, pH 7.0). After the cells were thawed and suspended, the resulting suspension was centrifuged and the supernatant discarded. The resulting cell pellet was resuspended in a total volume of 12 mL of this same phosphate buffer. Into a second 15-mL polypropylene centrifuge tube was weighed 0.1081 g (0.114 mL, 1.00 mmol, 0.100 M) of 2-methylglutaronitrile, then 9.89 mL of the *A. facilis* 72W (ATCC 55746) cell suspension (0.494 g wet cell weight) was added and the resulting suspension mixed on a rotating platform at 27° C. Samples (0.300 mL) were withdrawn and centrifuged, then 0.180 mL of the supernatant was placed in a Millipore Ultrafree-MC filter unit (10 K MWCO) and mixed with 0.020 mL of an aqueous solution of 0.750 M N-methylpropionamide (HPLC external standard solution). Sufficient 1.0 M HCl was added to lower the pH of the sample to ca. 2.5 and the resulting solution was filtered and analyzed by HPLC. After 1.0 h, the HPLC yields of 4-cyanopentanoic acid and 2-methylglutaric acid were 99.3% and 0.7%, respectively, with no 2-methylglutaronitrile remaining.

EXAMPLE 2 (COMPARATIVE)

4-Cyanopentanoic Acid (Ammonium Salt)

The procedure described in Example 1 was repeated using *Acidovorax facilis* 72W (ATCC 55746) cells which had not been heat-treated at 50° C. for 1 h before freezing. After 1.0 h, the HPLC yields of 4-cyanopentanoic acid and 2-methylglutaric acid were 62.7% and 34.6%, respectively, with no 2-methyl-glutaronitrile remaining.

EXAMPLE 3

4-Cyanopentanoic Acid (Ammonium Salt)

First, 1.136 grams (wet cell weight) of frozen *Acidovorax facilis* 72W (ATCC 55746) cells (previously heat-treated at 50° C. for 1 h before freezing) were placed into a 50-mL polypropylene centrifuge tube, followed by 21.6 mL of potassium phosphate buffer (20 mM, pH 7.0). After the cells were thawed and suspended, the resulting suspension was centrifuged and the supernatant discarded. The resulting cell pellet was resuspended in a total volume of 22.7 mL of this same phosphate buffer. Into a 15-mL polypropylene centrifuge tube was weighed 0.4355 g (0.458 mL, 4.00 mmol, 0.403 M) of 2-methyl-glutaronitrile, then 9.54 mL of the *A. facilis* 72W (ATCC 55746) cell suspension (0.477 g wet cell weight) was added and the resulting suspension mixed on a rotating platform at 27° C. Samples (0.300 mL) were diluted 1:4 with distilled water, then centrifuged, and 0.180 mL of the supernatant was placed in a Millipore Ultrafree-MC filter unit (10 K MWCO) and mixed with 0.020 mL of an aqueous solution of 0.750 M N-methylpropionamide (HPLC external standard solution). Sufficient 1.0 M HCl was added to lower the pH of the sample to ca. 2.5 and the resulting solution was filtered and analyzed by HPLC. After 4.0 h, the HPLC yields of 4-cyanopentanoic acid and 2-methylglutaric acid were 99.4% and 0.6%, respectively, with no 2-methylglutaronitrile remaining.

EXAMPLE 4

4-Cyanopentanoic Acid (Ammonium Salt)

The procedure described in Example 3 was repeated, except that 1.086 g (1.143 mL, 10.04 mmol, two-phase reaction, 1.00 M product) of 2-methyl-glutaronitrile was mixed with 8.86 mL of the heat-treated *A. facilis* 72W (ATCC 55746) cell suspension (0.443 g wet cell weight) was mixed in a 15 mL polypropylene centrifuge tube on a rotating platform at 27° C. Samples (0.300 mL) were diluted 1:10 with distilled water, then centrifuged, and 0.180 mL of the supernatant was placed in a Millipore Ultrafree-MC filter unit (10 K MWCO) and mixed with 0.020 mL of an aqueous solution of 0.750 M N-methylpropionamide (HPLC external standard solution). Sufficient 1.0 M HCl was added to lower the pH of the sample to ca. 2.5, and the resulting solution was filtered and analyzed by HPLC. After 15.25 h, the HPLC yields of 4-cyanopentanoic acid and 2-methylglutaric acid were 98.7% and 1.3%, respectively, with no 2-methylglutaronitrile remaining.

EXAMPLE 5

4-Cyanopentanoic Acid (Ammonium Salt)

The procedure described in Example 1 was repeated using a suspension of *Acidovorax facilis* mutant strain 72-PF-15 (ATCC 55747) which had not been heat-treated at 50° C. for 1 h. After 3.0 h, the HPLC yields of 4-cyanopentanoic acid and 2-methylglutaric acid were 96.8% and 3.6%, respectively, with no 2-methylglutaronitrile remaining.

EXAMPLE 6

4-Cyanopentanoic Acid (Ammonium Salt)

The procedure described in Example 3 was repeated using a suspension of *Acidovorax facilis* mutant strain 72PF-15 (ATCC 55747) which had not been heat-treated at 50° C. for 1 h. A mixture of 0.4355 g (0.458 mL, 4.00 mmol, 0.403 M) of 2-methylglutaronitrile and 9.54 mL of the *A. facilis* mutant strain 72-PF-15 cell suspension (0.477 g wet cell weight) was mixed in a 15 mL polypropylene centrifuge tube on a rotating platform at 27° C. After 6.0 h, the HPLC yields of 4-cyanopentanoic acid and 2-methylglutaric acid were 98.8% and 1.2%, respectively, with no 2-methylglutaronitrile remaining.

EXAMPLE 7

4-Cyanopentanoic Acid (Ammonium Salt)

The procedure described in Example 4 was repeated using a suspension of *Acidovorax facilis* mutant strain 72-PF-15 (ATCC 55747) which had not been heat-treated at 50° C. for 1 h. A mixture of 1.086 g (1.143 mL, 10.04 mmol, 1.00 M) of 2-methylglutaronitrile and 8.86 mL of the *A. facilis* mutant strain 72PF-15 (ATCC 55747) cell suspension (0.443 g wet cell weight) was mixed in a 15 mL polypropylene centrifuge tube on a rotating platform at 27° C. After 15.25 h, the HPLC yields of 4-cyanopentanoic acid and 2-methylglutaric acid were 99.2% and 0.8%, respectively, with no 2-methylglutaronitrile remaining.

EXAMPLE 8

4-Cyanopentanoic Acid Isolation

Into a 2-L erlenmeyer flask equipped with a magnetic stir bar was weighed 150 g (wet cell weight) of frozen *Acidovorax facilis* 72W (ATCC 55746) (not previously heat-treated at 50° C. for 1 h before freezing). Potassium phosphate buffer (20 mM, pH 7.0) was then added to a total volume of 1.50 L. After the cells were thawed and suspended, the resulting suspension was heated in a water bath to 50° C. for 1 h, then cooled to 10° C. in an ice/water bath, centrifuged, and the supernatant discarded. The resulting cell pellet was washed once by resuspension in 1.50 L of the same phosphate buffer, followed by centrifugation. The washed cell pellet was transferred to a 4-L erlenmeyer flask equipped with magnetic stir bar, then suspended in a total volume of 2.5 L of potassium phosphate buffer (20 mM, pH 7.0). With stirring, 129.6 g (136.4 mL, 1.20 mol, 0.400 M) of 2-methylglutaronitrile was added, and the final volume adjusted to 3.00 L with the same phosphate buffer. The mixture was stirred at 25° C., and samples were withdrawn at regular intervals and analyzed by HPLC. After 21.5 h, the HPLC yields of 4-cyanopentanoic acid (4-CPA) and 2-methylglutaric acid were 99.5% and 0.5%, respectively, with no 2-methylglutaronitrile remaining.

The reaction mixture was centrifuged, the cell pellet recovered for reuse, and the resulting supernatant decanted and filtered using an Amicon 2.5 L Filter Unit equipped with a YM-10 filter (10 K MWCO). The filtrate was placed in a 4.0 L flask, and the pH of the solution adjusted to 2.5 with 6 N HCl. To the solution was then added sodium chloride with stirring until saturated; then 1.0 L portions of the resulting solution were extracted with 4×500 ML of ethyl ether. The combined ether extracts were dried (MgSO$_4$), filtered, and the solution concentrated to 1.0 L by rotary evaporation at reduced pressure. To the solution 15 was then added 1.2 L of hexane and 0.200 mL of ethyl ether, and the resulting solution cooled to −78° C. The resulting white crystalline solid was isolated by rapid vacuum filtration and washing with 300 mL of cold (5° C.) hexane. Residual solvent was removed under high vacuum (150 millitorr) to yield 120.3 g (79% isolated yield) of 4-cyanopentanoic acid (mp. 31.9–32.6° C.).

EXAMPLE 9

4-Cyanopentanoic Acid (Ammonium Salt)

The recovered cell pellet from the Example 8 was reused in several consecutive 3.0-L batch reactions for the hydrolysis of 2-methylglutaronitrile to 4-cyanopentanoic acid ammonium salt. At concentrations of 2-methylglutaronitrile greater than 0.400 M, the solubility of the dinitrile in the aqueous cell suspension was exceeded, and these reactions ran as two-phase aqueous/organic mixtures until the remaining 2-methylglutaronitrile was soluble in the reaction mixture. The Table below lists the final concentration of 4-CPA ammonium salt produced, and the percent yields of 4-CPA and 2-methylglutaric acid. Based on dry weight of cell catalyst (1 gram wet weight=0.20 gram dry weight), 86 g 4-CPA/g dry weight of *Acidovorax facilis* 72W (ATCC 55746) was produced.

| rxn # | Time (h) | [4-CPA(NH$_4$)] (M) | 4-CPA (% yield) | 2-MGA (% yield) |
|---|---|---|---|---|
| 1 | 23 | 0.40 | 99.5 | 0.5 |
| 2 | 22 | 0.40 | 99.1 | 0.9 |
| 3 | 46 | 1.00 | 99.2 | 0.8 |
| 4 | 50 | 1.00 | 99.4 | 0.6 |
| 5 | 99 | 1.85 | 98.8 | 1.2 |
| 6 | 261 | 2.00 | 98.9 | 1.1 |

EXAMPLE 10

3-Cyanopentanoic Acid (Ammonium Salt)

First, 0.60 grams (wet cell weight) of frozen *Acidovorax facilis* 72W (ATCC 55746) (previously heat-treated at 50° C. for 1 h before freezing) was placed into a 15-mL polypropylene centrifuge tube, and then followed by the addition of 10 mL of potassium phosphate buffer (20 mM, pH 7.0). After the cells were thawed and suspended, the resulting suspension was centrifuged, and the supernatant discarded. The resulting cell pellet was resuspended in a total volume of 10 mL of this same phosphate buffer. Into a second 15-mL polypropylene centrifuge tube was weighed 0.1080 g (0.112 mL, 1.00 mmol, 0.100 M) of 2-ethylsuccinonitrile, 8.00 mL of the *A. facilis* 72W cell suspension (0.5 g wet cell weight) was added, the total volume adjusted to 10.0 mL with potassium phosphate buffer (20 mM, pH 7.0), and the resulting suspension mixed on a rotating platform at 27° C. Samples (0.300 mL) were withdrawn and centrifuged, then 0.180 mL of the supernatant was placed in a Millipore Ultrafree-MC filter unit (0.22 micron) and mixed with 0.020 mL of an aqueous solution of 0.750 M N-methylpropionamide (HPLC external standard solution). The resulting solution was filtered and analyzed by HPLC. After 1.0 h, the HPLC yield of 3-cyanopentanoic acid was 100%, with no 2-ethylsuccinonitrile remaining, and no other byproducts observed.

EXAMPLE 11

3-Cyanopentanoic Acid (Ammonium Salt)

The procedure described in Example 10 was repeated, using 0.4337 g (0.449 mL, 4.01 mmol, 0.401 M) of 2-ethylsuccinonitrile and 8.00 mL of the heat-treated *A. facilis* 72W (ATCC 55746) cell suspension (0.5 g wet cell weight), in a total volume of 10.0 mL (adjusted with potassium phosphate buffer (20 mM, pH 7.0)). Samples (0.100 mL) were withdrawn, diluted 1:4 with water and centrifuged; 0.180 mL of the supernatant was then placed in a Millipore Ultrafree-MC filter unit (0.22 micron) and mixed with 0.020 mL of an aqueous solution of 0.750 M N-methylpropionamide (HPLC external standard solution). The resulting solution was filtered and analyzed by HPLC. After 8.0 h, the HPLC yield of 3 -cyanopentanoic acid was 100%, with no 2-ethylsuccinonitrile remaining, and no other byproducts observed.

EXAMPLE 12

3-Cyanopentanoic Acid (Ammonium Salt)

The procedure described in Example 10 was repeated, using 1.087 g (1.13 mL, 10.1 mmol, two-phase reaction, 1.01 M product) of 2-ethylsuccinonitrile and 8.00 mL of the heat-treated *A. facilis* 72W (ATCC 55746) cell suspension (0.5 g wet cell weight), in a total volume of 10.0 mL (adjusted with potassium phosphate buffer (20 mM, pH 7.0)). Samples (0.100 mL) were withdrawn, diluted 1 :10 with water and centrifuged, then 0.180 mL of the supernatant was placed in a Millipore Ultrafree-MC filter unit (0.22 micron) and mixed with 0.020 mL of an aqueous solution of 0.750 M N-methylpropionamide (HPLC external standard solution). The resulting solution was filtered and analyzed by HPLC. After 71 h, the HPLC yield of 3-cyanopentanoic acid was 100%, with no 2-ethylsuccinonitrile remaining, and no other byproducts observed.

EXAMPLE 13

3-Cyanopentanoic Acid Isolation

Into a 4.0 L erlenmeyer flask equipped with magnetic stir bar was placed 161 g of frozen Acidovorax facilis 72W (ATCC 55746) cells (previously heat-treated at 50° C. for 1 h before freezing) and 1.60 L of potassium phosphate buffer (20 mM, pH 7.0) at 27° C. With stirring, the cells were thawed and suspended, then 325 g (336.0 mL, 3.00 mole) of 2-ethylsuccinonitrile was added with stirring, and the total volume of the mixture adjusted to 2.40 L with potassium phosphate buffer (20 mM, pH 7.0). The resulting mixture was stirred at 27° C., and samples (0.100 mL) were withdrawn, diluted 1:10 with water and centrifuged, 0.180 mL of the supernatant was then placed in a Millipore Ultrafree-MC filter unit (0.22 micron) and mixed with 0.020 mL of an aqueous solution of 0.750 M N-methylpropionamide (HPLC external standard solution). The resulting solution was filtered and analyzed by HPLC. After 183 h, the HPLC yield of 3-cyanopentanoic acid was 100%, with no 2-ethylsuccinonitrile remaining, and no other byproducts observed. The reaction mixture was centrifuged, the cell pellet recovered for reuse, and the resulting 2.3 L of supernatant decanted and filtered using an Amicon 2.5 L Filter Unit equipped with a YM-10 filter (10K MWCO). The concentration of 3-cyanopentanoic acid ammonium salt in the filtrate was 1.26 M.

A 300-mL portion of the filtrate described above, containing 1.26 M 3-cyanopentanoic acid ammonium salt, was adjusted to pH 2.5 with ca. 60 mL of 6 N HCl, then saturated with sodium chloride and extracted with 4×200 mL of ethyl ether. The combined organic extracts were dried over magnesium sulfate, filtered, and the solvent removed by rotary evaporation at reduced pressure at 28° C. The resulting slightly-yellow viscous oil was stirred under high vacuum (50 millitorr) to remove residual solvent at 28° C., then cooled to −20° C. for 2–3 h to produce 3-cyanopentanoic acid as a crystalline white solid (45.9 g, 96% yield); m.p. 33.0–34.0° C.

EXAMPLE 14

3-Cyanopentanoic Acid (Ammonium Salt)

The procedure described in Example 10 was repeated using a suspension of *Acidovorax facilis* mutant strain 72-PF-15 (ATCC 55747) which had not been heat-treated at 50° C. After 1.0 h, the HPLC yield of 3-cyanopentanoic acid was 100%, with no 2-ethylsuccinonitrile remaining, and no other byproducts observed.

EXAMPLE 15

3-Cyanopentanoic Acid (Ammonium Salt)

The procedure described in Example 14 was repeated using 0.4325 g (0.455 mL, 4.00 mmol, 0.400 M) of 2-ethylsuccinonitrile and 8.00 mL (0.5 g wet cell weight) of a suspension of *Acidovorax facilis* mutant strain 72-PF-15 (ATCC 55747) which had not been heat-treated at 50° C., in a total volume of 10.0 mL (adjusted with potassium phosphate buffer (20 mM, pH 7.0)). After 25 h, the HPLC yield of 3-cyanopentanoic acid was 100%, with no 2-ethylsuccinonitrile remaining, and no other byproducts observed.

EXAMPLE 16

3-Cyanopentanoic Acid (Ammonium Salt)

The procedure described in Example 14 was repeated, using 1.087 g (1.14 mL, 10.1 mmol, two-phase reaction, 1.01 M product) of 2-ethyl-succinonitrile and 8.00 mL (0.5 g wet cell weight) of a suspension of *Acidovorax facilis* mutant strain 72-PF-15 (ATCC 55747) which had not been heat-treated at 50° C., in a total volume of 10.0 mL (adjusted with potassium phosphate buffer (20 mM, pH 7.0)). After 71 h, the HPLC yield of 3-cyanopentanoic acid was 76.6%, with 25.1% 2-ethylsuccinonitrile remaining, and no other byproducts observed.

EXAMPLE 17

4-Cyano-4-Pentenoic Acid Isolation

Into a 500 mL erlenmeyer flask equipped with magnetic stir bar was placed 50.0 g of frozen *Acidovorax facilis* 72W (ATCC 55746) cells (previously heat-treated at 50° C. for 1 h before freezing) and 450 mL of potassium phosphate buffer (20 mM, pH 7.0) at 27° C. With stirring, the cells were thawed and suspended, then centrifuged and the supernatant discarded. The cell pellet was resuspended in a total volume of 863 mL of potassium phosphate buffer (20 mM, pH 7.0) in a 1.0 L flask, then 133 g (137.0 mL, 1.25 mole) of 2-methyleneglutaronitrile was added with stirring at 27° C. At concentrations of 2-methyleneglutaronitrile greater than 0.400 M, the solubility of the dinitrile in the aqueous cell suspension was exceeded, and these reactions ran as two-phase aqueous/organic mixtures until the remaining 2-methyleneglutaronitrile was soluble in the reaction mixture. Samples (0.100 mL) were withdrawn, diluted 1:10 with water and centrifuged, then 0.150 mL of the supernatant was placed in a Millipore Ultrafree-MC filter unit (0.22 micron) and mixed with 0.150 mL of an aqueous solution of 0.150 M N-methylpropionamide (HPLC external standard solution). The resulting solution was filtered and analyzed by HPLC. After 26 h, the HPLC yield of 4-cyano-4-pentenoic acid was 100%, with no 2-methyleneglutaronitrile remaining, and no other byproducts observed. The reaction mixture was centrifuged, the cell pellet was recovered for reuse, and the supernatant was filtered using an Amicon 2.5 L Filter Unit equipped with a YM-10 filter (10K MWCO). The final concentration of 4-cyano-4-pentenoic acid ammonium salt in the filtrate was 1.298 M.

A 100-mL portion of the filtrate containing the 4-cyano-4-pentenoic acid ammonium salt product mixture described above was adjusted to pH 2.7 with 6 N HCl, then saturated with sodium chloride and extracted with 4×100 mL of ethyl ether. The combined organic extracts were dried over magnesium sulfate, filtered, and the volume of the combined extracts reduced to 100 mL by rotary evaporation at reduced pressure at 28° C. To the ether solution was added 200 mL of hexane, and the resulting solution cooled to −78° C. The resulting white solid which crystallized was isolated by rapid vacuum filtration and washing with 100 mL of cold (5° C.) hexane. Residual solvent was removed under high vacuum (150 millitorr) to yield 9.80 g (60% isolated yield) of 4-cyano-4-pentenoic acid (m.p. 26.5–27.0° C., stored at −20° C.).

EXAMPLE 18

4-Cyano-4-Pentenoic (Ammonium Salt)

The recovered cell pellet from the Example 17 (*Acidovorax facilis* 72W (ATCC 55746) cells) was reused in a second consecutive 1.0-L batch reactions for the hydrolysis of 2-methyleneglutaronitrile to 4-cyano-4-pentenoic acid ammonium salt. At concentrations of 2-methyleneglutaronitrile greater than 0.400 M, the solubility of the dinitrile in the aqueous cell suspension was exceeded, and these reactions ran as two-phase aqueous/organic mixtures until the remaining 2-methyleneglutaronitrile was soluble in the reaction mixture. The cell pellet was resuspended in a total volume of 781 ml of potassium phosphate buffer (20 mM, pH 7.0) in a 1.0 L flask, then 212 g (219.0 mL, 2.00 mole) of 2-methyleneglutaronitrile was added with stirring at 27° C. Samples (0.100 mL) were withdrawn, diluted 1:20 with water and centrifuged, then 0.150 mL of the supernatant was placed in a Millipore Ultrafree-MC filter unit (0.22 micron) and mixed with 0.150 mL of an aqueous solution of 0.150 M N-methylpropionamide (HPLC external standard solution). The resulting solution was filtered and analyzed by HPLC. After 53 h, the HPLC yield of 4-cyano-4- pentenoic acid was 100%, with no 2-methyleneglutaronitrile remaining, and no other byproducts observed.

EXAMPLE 19

3-Cyanopropanoic Acid (Ammonium Salt)

First, 0.50 grams (wet cell weight) of frozen Acidovorax facilis 72W (ATCC 55746) (previously heat-treated at 50° C. for 1 h before freezing) were placed into a 15-mL polypropylene centrifuge tube and followed by the addition of 10 mL of potassium phosphate buffer (20 mM, pH 7.0). After the cells were thawed and suspended, the resulting suspension was centrifuged, and the supernatant discarded. The resulting cell pellet was resuspended in a total volume of 10 mL of this same phosphate buffer. Into a second 15-mL polypropylene centrifuge tube was placed 0.3236 g (4.00 mmol, 0.400 M) of succinonitrile dissolved in a total volume of 8.0 mL of potassium phosphate buffer (20 mM, pH 7.0), then 2.00 mL of the *A. facilis* 72W (ATCC 55746) cell suspension (0.10 g wet cell weight) was added, and the resulting suspension mixed on a rotating platform at 27° C. Samples (0.100 mL) were withdrawn, diluted 1:4 with water and centrifuged, then 0.150 mL of the supernatant was placed in a Millipore Ultrafree-MC filter unit (0.22 micron) and mixed with 0.015 mL of 0.1 M HCl and 0.150 mL of an aqueous solution of 0.100 M propionic acid (HPLC external standard solution). The resulting solution was filtered and analyzed by HPLC. After 3.0 h, the HPLC yield of 3-cyanopropanoic acid was 100%, with no succinonitrile remaining, and no other byproducts observed.

EXAMPLE 20

3-Cyanopropanoic Acid Isolation

Into a 500 mL erlenmeyer flask equipped with magnetic stir bar was placed 20.0 g of frozen *Acidovorax facilis* 72W (ATCC 55746) cells (heat-treated at 50° C. for 1 h before freezing) and 200 mL of potassium phosphate buffer (20 mM, pH 7.0) at 27° C. With stirring, the cells were thawed and suspended, then centrifuged and the supernatant discarded. This wash procedure was repeated. The resulting cell pellet was resuspended in a total volume of 1.00 L of potassium phosphate buffer (20 mM, pH 7.0) containing 101.1 g (1.25 mole, 1.25 M) succinonitrile and the resulting mixture was stirred in a 1 -L flask placed in a water bath at 27° C. Samples (0.100 mL) were withdrawn, diluted 1: 10 with water and centrifuged, then 0.150 mL of the supernatant was placed in a Millipore Ultrafree-MC filter unit (0.22 micron) and mixed with 0.015 mL of 0.1 M HCl and 0.150 mL of an aqueous solution of 0.100 M propionic acid (HPLC external standard solution). The resulting solution was filtered and analyzed by HPLC. After 1.0 h, the HPLC yield of 3-cyanopropanoic acid and succinic acid were 99.7% and 0.3%, respectively, with no succinonitrile remaining. The reaction mixture was centrifuged, and the supernatant was filtered using an Amicon 2.5 L Filter Unit equipped with a YM-10 filter (10K MWCO). The final concentration of 3-cyanopropanoic acid ammonium salt in the filtrate was 1.31 M.

A 200-mL portion of the filtrate containing the 3-cyanopropanoic acid ammonium salt product mixture described above was adjusted to pH 2.5 with 6 N HCl, then saturated with sodium chloride and extracted with 4×200 mL of ethyl ether. The combined organic extracts were dried over magnesium sulfate, filtered, and the solvent removed by rotary evaporation at reduced pressure. The resulting colorless oil was dissolved in 150 mL of ethyl ether, then 100 mL of hexane was added, and the resulting solution cooled to −78° C. The resulting white solid which crystallized was isolated by vacuum filtration, and residual solvent was removed under high vacuum (150 millitorr) to yield 14.32 g (55% isolated yield) of 3-cyanopropanoic acid (m.p. 49.5–51.0° C.).

EXAMPLE 21

4-Cyanobutyric Acid (Ammonium Salt)

First, 0.50 grams (wet cell weight) of frozen *Acidovorax facilis* 72W (ATCC 55746) (previously heat-treated at 50° C. for 1 h before freezing) were placed into a 15-mL polypropylene centrifuge tube and then followed by the addition of 10 mL of potassium phosphate buffer (20 mM, pH 7.0). After the cells were thawed and suspended, the resulting suspension was centrifuged, and the supernatant discarded. The resulting cell pellet was resuspended in a total volume of 10 mL of this same phosphate buffer. Into a second 15-mL polypropylene centrifuge tube was placed 0.3830 g (4.03 mmol, 0.400 M) of glutaronitrile dissolved in a total volume of 6.0 mL of potassium phosphate buffer (20 mM, pH 7.0), then 4.00 mL of the *A. facilis* 72W (ATCC 55746) cell suspension (0.20 g wet cell weight) was added, and the resulting suspension mixed on a rotating platform at 27° C. Samples (0.100 mL) were withdrawn, diluted 1:4 with water and centrifuged, then 0.150 mL of the supernatant was placed in a Millipore Ultrafree-MC filter unit (0.22 micron) and mixed with 0.015 mL of 0.1 M HCl and 0.150 mL of an aqueous solution of 0.150 M potassium acetate (HPLC external standard solution). The resulting solution was filtered and analyzed by HPLC. After 4.0 h, the HPLC yield of 4-cyanobutyric acid and glutaric acid were 85.1% and 8.2%, respectively, with 5.7% glutaronitrile remaining.

EXAMPLE 22

4-Cyanobutyric Acid Isolation

Into a 250 mL erlenmeyer flask equipped with magnetic stir bar was placed 15.0 g of frozen Acidovorax facilis 72W (ATCC 55746) cells (heat-treated at 50° C. for 1 h before freezing) and 135 mL of potassium phosphate buffer (20 mM, pH 7.0) at 27° C. With stirring, the cells were thawed and suspended, then centrifuged and the supernatant discarded. This wash procedure was repeated. The resulting cell pellet was resuspended in a total volume of 100 mL of potassium phosphate buffer (20 mM, pH 7.0) and this cell suspension was added to a 500 mL flask containing a magentic stir bar, 42.78 g (0.450 mole) of glutaronitrile and 157.2 mL of potassium phosphate buffer (20 mM, pH 7.0). The resulting mixture, containing 1.5 M glutaronitrile, was stirred at 27° C. Samples (0.100 mL) were withdrawn, diluted 1:10 with water and centrifuged. Then, 0.200 mL of the supernatant was placed in a Millipore Ultrafree-MC filter unit (0.22 micron) and mixed with 0.020 mL of 0.1 M HCl and 0.200 mL of an aqueous solution of 0.150 M potassium acetate (HPLC external standard solution). The resulting solution was filtered and analyzed by HPLC. After 4.0 h, the HPLC yield of 4-cyanobutyric acid ammonium salt and glutaric acid diammonium salt were 92.3% and 7.7%, respectively, with no glutaronitrile remaining.

The reaction mixture was centrifuged and the supernatant was filtered using an Amicon 2.5 L Filter Unit equipped with a YM-10 filter (10K MWCO). The filtrate containing the 4-cyanobutyric acid ammonium salt product mixture described above was adjusted to pH 3.5 with 6 N HCl, then saturated with sodium chloride and extracted with 4×300 mL of ethyl ether. The combined organic extracts were dried over magnesium sulfate, filtered, and the solvent removed by rotary evaporation at reduced pressure followed by stirring under vacuum (100 millitorr) to yield 35.3 g (62% yield) of 4-cyanobutyric acid as a pale yellow oil which crystallized upon standing. The solid was recrystallized from 1:1 ethyl acetate/hexane at 5° C. (mp. 39.6–40.2° C.).

EXAMPLE 23

5-Cyanopentanoic Acid (Ammonium Salt)

First, 2.0 grams (wet cell weight) of frozen *Comamonas testosteroni* 5-MGAM-4D (ATCC 55744) cells (previously heat-treated at 50° C. for 1 h before freezing) were placed into a 50-mL polypropylene centrifuge tube and followed by the addition of 30 mL of potassium phosphate buffer (20 mM, pH 7.0). After the cells were thawed and suspended, the resulting suspension was centrifuged, and the supernatant discarded. The resulting cell pellet was resuspended in a total volume of 30 mL of this same phosphate buffer. Into a second 15-mL polypropylene centrifuge tube was weighed 0.1085 g (0.114 mL, 1.00 mmol, 0.100 M) of adiponitrile, then 9.29 mL of potassium phosphate buffer (20 mM, pH 7.0) and 0.60 mL of the *Comamonas testosteroni* 5-MGAM-4D (ATCC 55744) cell suspension (0.040 g wet cell weight) was added, and the resulting suspension mixed on a rotating platform at 27° C. Samples (0.300 mL) were withdrawn and centrifuged, then 0.180 mL of the supernatant was placed in a Millipore Ultrafree-MC filter unit (10 K MWCO) and mixed with 0.020 mL of an aqueous solution of 0.750 M N-ethylacetamide (HPLC external standard solution) and sufficient 1.0 M HCL to lower the pH of the sample to ca. pH 2.5. The resulting solution was filtered and analyzed by HPLC. After 5.0 h, the HPLC yield of 5-cyanopentanoic acid, adipamic acid, adipamide, and adipic acid were 96.6%, 1.7%, 1.4% and 0.3%, with no adiponitrile remaining.

EXAMPLE 24

5-Cyanopentanoic Acid (Ammonium Salt)

The procedure described in Example 23 was repeated, using 0.4338 g (0.457 mL, 4.01 mmol, 0.401 M) of adiponitrile and 3.0 mL of the heat-treated *Comamonas testosteroni* 5-MGAM-4D (ATCC 55744) cell suspension (0.20 g wet cell weight), in a total volume of 10.0 mL (adjusted with potassium phosphate buffer (20 mM, pH 7.0)). Samples (0.100 mL) were withdrawn, diluted 1:4 with water and centrifuged, then 0.180 mL of the supernatant was placed in a Millipore Ultrafree-MC filter unit (10 K MWCO) and mixed with 0.020 mL of an aqueous solution of 0.750 M N-ethylacetamide (HPLC external standard solution) and sufficient 1.0 M HCl to lower the pH of the sample to ca. pH 2.5. The resulting solution was filtered and analyzed by HPLC. After 5.0 h, the HPLC yield of 5-cyanopentanoic acid, adipamic acid, adipamide, and adipic acid were 94.0%, 4.0%, 0.6% and 1.4%, with no adiponitrile remaining.

EXAMPLE 25

5-Cyanopentanoic Acid (Ammonium Salt)

The procedure described in Example 23 was repeated, using 1.084 g (1.14 mL, 10.0 mmol, two-phase reaction, 1.00 M product) of adiponitrile and 7.5 mL of the heat-treated *Comamonas testosteroni* 5-MGAM-4D (ATCC 55744) cell suspension (0.50 g wet cell weight), in a total volume of 10.0 mL (adjusted with potassium phosphate buffer (20 mM, pH 7.0)). Samples (0.100 mL) were withdrawn, diluted 1:10 with water and centrifuged, then 0.1 80 mL of the supernatant was placed in a Millipore Ultrafree-MC filter unit (10 K MWCO) and mixed with 0.020 mL of an aqueous solution of 0.750 M N-ethylacetamide (HPLC external standard solution) and sufficient 1.0 M HCl to lower the pH of the sample to ca. pH 2.5. The resulting solution was filtered and analyzed by HPLC. After 24.0 h, the HPLC yield of 5-cyanopentanoic acid, adipamic acid, adipamide, and adipic acid were 90.0%, 4.2%, 0.0% and 5.7%, with no adiponitrile remaining.

EXAMPLE 26

5-Cyanopentanoic Acid Isolation

Into a 2-L erlenmeyer flask equipped with magnetic stir bar was placed a suspension of 4.0 g of *Comamonas testosteroni* 5-MGAM-4D (ATCC 55744) cells (previously heat-treated at 50° C. for 1 h) in 1.72 L of potassium phosphate buffer (20 mM, pH 7.0) at 27° C. To the suspension was then added with stirring 270.4 g (284.3 mL, 2.5 mole, ca. 1.25 M final product concentration) of adiponitrile, and the resulting mixture was stirred at 27° C. Samples (0.200 mL) were withdrawn, diluted 1:5 with water and centrifuged, then 0.200 mL of the supernatant was placed in a Millipore Ultrafree-MC filter unit (10 K MWCO) and sufficient 1.0 M HCl added to lower the pH of the sample to ca. pH 2.5. The resulting solution was filtered and analyzed by HPLC. After 63 h, the hydrolysis reaction had slowed considerably, so an additional 10.0 g of the same microbial cell catalyst was added to the mixture. After 86 h, the HPLC yield of 5-cyanopentanoic acid, adipamic acid, adipamide, and adipic acid were 88.2%, 4.7%, 6.6% and 0.0%, with no adiponitrile remaining. The reaction mixture was centrifuged, and the supernatant was filtered using an Amicon 2.5 L Filter Unit equipped with a YM-10 filter (10K MWCO).

A 200-mL portion of the filtrate of the product mixture described above, containing the 5-cyanopentanoic acid ammonium salt (1.13 M), was adjusted to pH 2.5 with 6 N HCl, then saturated with sodium chloride and extracted with 4×200 mL of ethyl ether. The combined ether extracts were dried over magnesium sulfate, filtered, and the solvent removed by rotary evaporation at reduced pressure. Remaining ether was removed by stirring the colorless liquid at room temperature under high vacuum (60 millitorr) for 5 h to yield 27.32 g (95% isolated yield) of 5-cyanopentanoic acid. The 5-cyanopentanoic acid was then distilled under vacuum (75 millitorr) at 110–112° C. without decomposition.

EXAMPLE 27

5-Methyl-2-Piperidone from 4-Cyanopentanoic Acid Ammonium Salt

Into a 100 mL graduated cylinder was placed 54.4 mL of an aqueous reaction mixture containing 1.85 M 4-cyanopentanoic acid ammonium salt (0.1 mole 4-cyanopentanoic acid ammonium salt, produced by the enzymatic hydrolysis of 2-methylglutaronitrile; Example 9, filtered product mixture from reaction #5), then 12.9 mL of concentrated ammonium hydroxide (29.3% $NH_3$, 0.2 mole $NH_3$) was added and the final volume adjusted to 100 mL with distilled water. The final concentrations of 4-cyanopentanoic acid ammonium salt and added ammonium hydroxide were 1.0 M and 2.0 M, respectively. To the resulting solution was added 0.631 g (5 wt. %/wt. of 4-cyanopentanoic acid) of chromium-promoted Raney Nickel (Grace Davison Raney® 2400 Active Metal Catalyst), and the resulting mixture charged to a 300-mL 314 SS Autoclave Engineers EZE-Seal stirred autoclave equipped with a Dispersimax® turbine-type impeller. After flushing the reactor with nitrogen, the contents of the reactor were stirred at 1000 rpm and heated at 160° C. under 500 psig of hydrogen gas for 3 h. After cooling to room temperature, analysis of the final reaction mixture by gas chromatography indicated a 96.4% yield of 5-methyl-2-piperidone, with no 4-cyanopentanoic acid ammonium salt remaining.

The product mixture was filtered to remove the catalyst, then adjusted to pH 6.0 with 6 N HCl and saturated with sodium chloride. The resulting solution was extracted five times with 100 mL of dichloro-methane, and the combined organic extracts dried over magnesium sulfate, filtered, and the solvent removed by rotary evaporation under reduced pressure to yield a colorless oil. After removal of the remaining solvent under vacuum (0.1 mm Hg), the oil crystallized to form a white solid, which was recrystallized from 150 mL of ethyl ether at −78° C. to yield 6.69 g (59% isolated yield) of 5-methyl-2-piperidone (mp 55.5–56.2° C.).

EXAMPLE 28

5-Methyl-2-Piperidone from 4-Cyanopentanoic Acid

The reaction described in Example 27 was repeated using 12.71 g (0.100 mole) of crystalline 4-cyanopentanoic acid (from an isolation described in Example 8) and 19.34 mL of concentrated ammonium hydroxide (29.3% $NH_3$, 0.3 mole $NH_3$) in a total volume of 100 mL. The final concentrations of 4-cyanopentanoic acid ammonium salt and ammonia were 1.0 M and 2.0 M, respectively. Analysis of the final reaction mixture by gas chromatography indicated a 91.1% yield of 5-methyl-2-piperidone, with no 4-cyanopentanoic acid remaining.

EXAMPLE 29

5-Methyl-2-Piperidone from 4-Cyanopentanoic Acid Ammonium Salt

Hydrogenations of 5-mL aqueous reaction mixtures containing 1.0 M 4-cyanopentanoic acid ammonium salt (filtered product mixture from Example 9, reaction #5), 0 to 3.0 M ammonium hydroxide, and 5 wt. % or 10 wt. % (relative to weight of 4-cyanopentanoic acid) of a hydrogenation catalyst selected from a group consisting of Cr-promoted Raney nickel catalyst (Raney 2400), 5% palladium on carbon, 10% palladium on carbon, 5% ruthenium on alumina, or 10% ruthenium on alumina were run in glass shaker tubes at 500 psig hydrogen gas and at either 160° C. or 180° C. were examined for the production of the corresponding lactam 5-methyl-2-piperidone (5-MPPD):

| Temp. (° C.) | catalyst | [NH$_4$OH] (M) | wt. % catalyst | Time (h) | % 4-CPA conversion | 5-MPPD (%) |
|---|---|---|---|---|---|---|
| 160 | Raney 2400 | 0 | 5 | 2 | 100 | 85.6 |
| 160 | Raney 2400 | 2.0 | 5 | 3 | 100 | 96.4 |
| 160 | Raney 2400 | 3.0 | 5 | 2 | 100 | 86.5 |
| 160 | 5% Pd/C | 2.0 | 5 | 2 | 10 | 0 |
| 160 | 10% Pd/C | 2.0 | 5 | 2 | 14 | 0 |
| 160 | 5% Ru/Al$_2$O$_3$ | 2.0 | 5 | 2 | 15 | 0 |
| 160 | 10% Ru/Al$_2$O$_3$ | 2.0 | 5 | 2 | 20 | 0 |
| 180 | Raney 2400 | 2.0 | 5 | 2 | 100 | 91.4 |
| 180 | Raney 2400 | 3.0 | 5 | 2 | 100 | 89.5 |

EXAMPLE 30

4-Ethylpyrrolidin-2-One from 3-Cyanopentanoic Acid Ammonium Salt

Into a 100 mL graduated cylinder was placed 79.4 mL of an aqueous reaction mixture containing 1.26 M 3-cyanopentanoic acid ammonium salt (0.1 mole 3-cyanopentanoic acid ammonium salt, produced by the enzymatic hydrolysis of 2-ethylsuccinonitrile; Example 13 filtered product mixture), then 12.9 mL of concentrated ammonium hydroxide (29.3% NH3, 0.2mole NH3) was added and the final volume adjusted to 100 mL with distilled water. The final concentrations of 3-cyanopentanoic acid ammonium salt and added ammonium hydroxide were 1.0 M and 2.0 M, respectively. To the resulting solution was added 0.631 g (5 wt. %/wt. of 3-cyano-pentanoic acid) of chromium-promoted Raney Nickel (Grace Davison Raney® 2400 Active Metal Catalyst), and the resulting mixture charged to a 300-mL 314 SS Autoclave Engineers EZE-Seal stirred autoclave equipped with a Dispersimax® turbine-type impeller. After flushing the reactor with nitrogen, the contents of the reactor were stirred at 1000 rpm and heated at 160° C. under 500 psig of hydrogen gas for 4 h. After cooling to room temperature, analysis of the final reaction mixture by gas chromatography indicated a 90.7% yield of 4-ethylpyrrolidin-2-one, with no 3-cyanopentanoic acid ammonium salt remaining.

EXAMPLE 31

4-Ethylpyrrolidin-2-One from 3-Cyanopentanoic Acid

The reaction described in Example 30 was repeated using 12.71 g (0.100 mole) of crystalline 3-cyanopentanoic acid (from isolation described in Example 13) and 19.34 mL of concentrated ammonium hydroxide (29.3% $NH_3$, 0.3 mole $NH_3$) in a total volume of 100 mL. The final concentrations of 3-cyanopentanoic acid ammonium salt and added ammonium hydroxide were 1.0 M and 2.0 M, respectively. Analysis of the final reaction mixture (2 h reaction time) by gas chromatography indicated a 92.1% yield of 4-ethylpyrrolidin-2-one, with no 3-cyanopentanoic acid remaining.

The product mixture was filtered to remove the catalyst, then adjusted to pH 7.0 with 6 N HCl and saturated with sodium chloride. The resulting solution was extracted four times with 100 mL of dichloro-methane, and the combined organic extracts dried over magnesium sulfate, filtered, and the solvent removed by rotary evaporation under reduced pressure to yield a colorless oil. After removal of the remaining solvent under vacuum (0.1 mm Hg), the oil was dissolved in 150 mL of ethyl ether, which was then cooled to −78° C. After 1 h, the white solid which had crystallized was collected by vacuum filtration to yield a total of 8.96 g (79% isolated yield) of 4-ethylpyrrolidin-2-one (mp 40.5–41.5° C.).

EXAMPLE 32

4-Ethylpyrrolidin-2-One from 3-Cyanopentanoic Acid Ammonium Salt

The reaction described in Example 30 was repeated exactly as described except that the temperature employed for the hydrogenation was 140° C. Analysis of the final reaction mixture (4 h reaction time) by gas chromatography indicated a 87.2% yield of 4-ethylpyrrolidin-2-one, with no 3-cyanopentanoic acid remaining.

EXAMPLE 33

4-Ethylpyrrolidin-2-One from 3-Cyanopentanoic Acid Ammonium Salt

The reaction described in Example 30 was repeated exactly as described except that 1.262 g (10 wt. %/wt. of 3-cyano-pentanoic acid) of chromium-promoted Raney Nickel (Grace Davison Raney® 2400 Active Metal Catalyst) was employed. Analysis of the final reaction mixture (1.5 h reaction time) by gas chromatography indicated a 91.0% yield of 4-ethylpyrrolidin-2-one, with no 3-cyanopentanoic acid remaining.

EXAMPLE 34

4-Ethylpyrrolidin-2-One from 3-Cyanopentanoic Acid Ammonium Salt (Temperature Dependence)

Hydrogenations of 5-mL aqueous reaction mixtures containing 1.0 M 3-cyanopentanoic acid (3-CPA) ammonium salt (filtered product mixture from Example 13), 2.0 M ammonium hydroxide, and 5 wt. % or 10 wt. % of Cr-promoted Raney nickel catalyst (Raney 2400) (relative to weight of 3-cyanopentanoic acid) were run in glass shaker tubes at 500 psig hydrogen gas and at temperatures from 70° C. to 180° C. for 2 h, then analyzed by high pressure liquid chromatography for conversion of 3-CPA and by gas chromatography for the production of 4-ethylpyrrolidin-2-one:

| Temp. (° C.) | 3-CPA ammonium salt (M) | [NH$_4$OH] (M) | wt. % Raney Ni | Time (h) | 3-CPA (% conv.) | 4-EPRD (% yield) |
| --- | --- | --- | --- | --- | --- | --- |
| 70 | 1.0 | 2.0 | 5 | 2 | 7 | 1.5 |
| 120 | 1.0 | 2.0 | 5 | 2 | 55 | 22.7 |
| 140 | 1.0 | 2.0 | 5 | 2 | 71 | 55.4 |
| 140 | 1.0 | 2.0 | 10 | 2 | 100 | 89.9 |
| 160 | 1.0 | 2.0 | 5 | 2 | 100 | 90.1 |
| 160 | 1.0 | 2.0 | 10 | 2 | 100 | 91.3 |
| 180 | 1.0 | 2.0 | 5 | 2 | 100 | 86.1 |
| 180 | 1.0 | 2.0 | 10 | 2 | 100 | 90.0 |

EXAMPLE 35

4-Ethylpyrrolidin-2-One from 3-Cyanopentanoic Acid Ammonium Salt (NH$_4$OH Concentration Dependence)

Hydrogenations of 5-mL aqueous reaction mixtures containing 1.0 M 3-cyanopentanoic acid (3-CPA) ammonium salt (filtered product mixture from Example 13), from 0 M to 3.0 M ammonium hydroxide, and 5 wt. % of Cr-promoted Raney nickel catalyst (Raney 2400) (relative to weight of 3-cyanopentanoic acid) were run in glass shaker tubes at 500 psig hydrogen gas and at temperatures of 1 60° C. or 180° C. for 2 h, then analyzed by high pressure liquid chromatography for conversion of 3-CPA and by gas chromatography for the production of 4-ethylpyrrolidin-2-one:

| Temp. (° C.) | 3-CPA ammonium salt (M) | [NH$_4$OH] (M) | wt. % Raney Ni | Time (h) | 3-CPA (% conv.) | 4-EPRD (% yield) |
| --- | --- | --- | --- | --- | --- | --- |
| 160 | 1.0 | 0 | 5 | 2 | 99 | 80.1 |
| 160 | 1.0 | 1.0 | 5 | 2 | 99 | 87.6 |
| 160 | 1.0 | 2.0 | 5 | 2 | 100 | 90.1 |
| 160 | 1.0 | 3.0 | 5 | 2 | 100 | 85.4 |
| 180 | 1.0 | 0 | 5 | 2 | 100 | 75.1 |
| 180 | 1.0 | 1.0 | 5 | 2 | 100 | 85.8 |
| 180 | 1.0 | 2.0 | 5 | 2 | 100 | 88.5 |
| 180 | 1.0 | 3.0 | 5 | 2 | 100 | 90.0 |

EXAMPLE 36

4-Ethylpyrrolidin-2-One from 3-Cyanopentanoic Acid Ammonium Salt (3-CPA Concentration Dependence)

Hydrogenations of 5-mL aqueous reaction mixtures containing 1.0 M, 1.5 M, or 2.0 M 3-cyanopentanoic acid (3-CPA) (isolated from filtered product mixture, Example 13), and 2.0 M, 3.0 M, or 4.0 M ammonium hydroxide, respectively, were run using as catalyst 5 wt. % of Cr-promoted Raney nickel (Raney 2400) (relative to weight of 3-cyanopentanoic acid) in glass shaker tubes at 500 psig hydrogen gas and at temperatures of 160° C. or 180° C. for 2 h, then analyzed by high pressure liquid chromatography for conversion of 3-CPA and by gas chromatography for the production of 4-ethylpyrrolidin-2-one:

| Temp. (° C.) | 3-CPA ammonium salt (M) | [NH$_4$OH] (M) | wt. % Raney Ni | Time (h) | 3-CPA (% conv.) | 4-EPRD (% yield) |
| --- | --- | --- | --- | --- | --- | --- |
| 160 | 1.0 | 2.0 | 5 | 2 | 100 | 90.1 |
| 160 | 1.5 | 3.0 | 5 | 2 | 99 | 76.1 |
| 160 | 2.0 | 4.0 | 5 | 2 | 99 | 80.0 |
| 180 | 1.0 | 2.0 | 5 | 2 | 100 | 88.5 |
| 180 | 1.5 | 3.0 | 5 | 2 | 99 | 77.3 |
| 180 | 2.0 | 4.0 | 5 | 2 | 99 | 84.1 |

EXAMPLE 37

Caprolactam from 5-Cyanopentanoic Acid Ammonium Salt

Hydrogenations of 5-mL aqueous reaction mixtures containing 1.0 M 5-cyanopentanoic acid (5-CPA) ammonium salt (prepared from enzymatic hydrolysis of adiponitrile; filtered product mixture from Example 26), from 0 M to 2.5 M ammonium hydroxide, and 5 wt. % of Cr-promoted Raney nickel catalyst (Raney 2400) (relative to weight of 5-cyanopentanoic acid) were run in glass shaker tubes at 500 psig hydrogen gas and at temperatures of from 70° C. to 160° C. for 2 h, then analyzed by high pressure liquid chromatography for conversion of 5-CPA and by gas chromatography for the production of caprolactam:

| Temp. (° C.) | 5-CPA ammonium salt (M) | [NH$_4$OH] (M) | Time (h) | 5-CPA (% conv.) | caprolactam (% yield) |
|---|---|---|---|---|---|
| 70 | 1.0 | 0 | 2 | 100 | 0.7 |
| 70 | 1.0 | 1.0 | 2 | 100 | 0.7 |
| 70 | 1.0 | 1.5 | 2 | 94 | 0.8 |
| 70 | 1.0 | 2.0 | 2 | 84 | 0.8 |
| 70 | 1.0 | 2.5 | 2 | 99 | 0.8 |
| 120 | 1.0 | 0 | 2 | 99 | 0.9 |
| 120 | 1.0 | 1.0 | 2 | 100 | 0.9 |
| 120 | 1.0 | 1.5 | 2 | 97 | 1.0 |
| 120 | 1.0 | 2.0 | 2 | 97 | 1.1 |
| 160 | 1.0 | 0 | 2 | 97 | 2.5 |
| 160 | 1.0 | 1.0 | 2 | 84 | 2.3 |
| 160 | 1.0 | 1.5 | 2 | 97 | 3.0 |
| 160 | 1.0 | 2.0 | 2 | 95 | 2.7 |

The cyclization of the ammonium salt of 6-aminocaproic acid (6-ACA) in the aqueous product mixtures prepared by the hydrogenation of 5-CPA ammonium salt at 70° C. (as described above) was attempted at a higher temperature by first removing the hydrogenation catalyst by filtration, then heating the ca. 1.0 M 6-ACA ammonium salt reaction mixtures at 280° C. for 2 h:

| Temp. (° C.) | 6-ACA ammonium salt (M) (prepared as described above) | [NH$_4$OH] (M) | Time (h) | caprolactam (% yield) |
|---|---|---|---|---|
| 280 | 1.0 | 0 | 2 | 17.8 |
| 280 | 1.0 | 1.0 | 2 | 17.2 |
| 280 | 1.0 | 1.5 | 2 | 11.0 |
| 280 | 1.0 | 2.0 | 2 | 9.0 |
| 280 | 1.0 | 2.5 | 2 | 3.1 |

EXAMPLE 38

1,5-Dimethyl-2-Piperidone from 4-Cyanopentanoic Acid Ammonium Salt

Hydrogenations of 5-mL aqueous reaction mixtures containing 1.0 M 4-cyanopentanoic acid ammonium salt (filtered product mixture from Example 9, reaction #5), 3.0 M methylamine, and 5 wt. % or 10 wt. % (relative to weight of 4-cyanpentanoic acid) of a hydrogenation catalyst selected from a group consisting of Cr-promoted Raney nickel catalyst (Raney 2400), 5% palladium on carbon, 5% palladium on alumina, 5% ruthenium on alumina, or 4.5% palladium/0.5% platinum on carbon were run in glass shaker tubes at 500 psig hydrogen gas and at 160° C. for 2 h, then analyzed for the production of 1,5-dimethyl-2-piperidone (5-DMPD) and 5-methyl-2-piperidone (5-MPPD):

| Temp. (° C.) | catalyst | wt. % catalyst | Time (h) | 4-CPA (% conv.) | 5-DMPD (% yield) | 5-MPPD (% yield) |
|---|---|---|---|---|---|---|
| 160 | Raney 2400 | 5 | 2 | 100 | 19.2 | 68.5 |
| 160 | Raney 2400 | 10 | 2 | 100 | 21.7 | 69.1 |
| 160 | 5% Ru/Al$_2$O$_3$ | 5 | 2 | 100 | 19.0 | 63.5 |
| 160 | 5% Pd/C | 5 | 2 | 99 | 81.7 | 7.8 |
| 160 | 5% Pd/Al$_2$O$_3$ | 5 | 2 | 93 | 77.2 | 4.6 |
| 160 | 4.5% Pd/0.5% Pt/C | 5 | 2 | 97 | 77.8 | 6.2 |

EXAMPLE 39

1,5-Dimethyl-2-Piperidone from 4-Cyanopentanoic Acid Ammonium Salt

Hydrogenations of 5-mL aqueous reaction mixtures containing 1.0 M 4-cyanopentanoic acid ammonium salt (filtered product mixture from Example 9, reaction #5), from 1.0 M to 3.0 M methylamine, and 5 wt. % (relative to weight of 4-cyanopentanoic acid) of 5% palladium on carbon were run in glass shaker tubes at 500 psig hydrogen gas and at 140° C. for 2 h, then analyzed for the production of 1,5-dimethyl-2-piperidone (5-DMPD), 5-methyl-2-piperidone (5-MPPD), and 2-methylglutaric acid (2-MGA):

| Temp. (° C.) | catalyst | time (h) | [CH$_3$NH$_2$] (M) | 4-CPA (% conv.) | 5-DMPD (% yield) | 5-MPPD (% yield) | 2-MGA (% yield) |
|---|---|---|---|---|---|---|---|
| 140 | 5% Pd/C | 2 | 1.0 | 100 | 53.3 | 0 | 0.7 |
| 140 | 5% Pd/C | 2 | 1.25 | 100 | 65.8 | 0 | 0.7 |
| 140 | 5% Pd/C | 2 | 1.5 | 99 | 74.5 | 0 | 0.8 |
| 140 | 5% Pd/C | 2 | 2.0 | 98 | 80.2 | 0 | 1.0 |
| 140 | 5% Pd/C | 2 | 3.0 | 99 | 83.4 | 0 | 1.1 |

EXAMPLE 40

1,5-Dimethyl-2-Piperidone from 4-Cyanopentanoic Acid Ammonium Salt

Hydrogenations of 5-mL aqueous reaction mixtures containing 1.0 M 4-cyanopentanoic acid ammonium salt (filtered product mixture from Example 9, reaction #5), from 1.0 M to 4.0 M methylamine, and 5 wt. % (relative to weight of 4-cyanopentanoic acid) of 5% palladium on carbon were run in glass shaker tubes at 500 psig hydrogen gas and at 160° C. for 2 h, then analyzed for the production of 1,5-dimethyl-2-piperidone (5-DMPD), 5-methyl-2-piperidone (5-MPPD), and 2-methylglutaric acid (2-MGA):

| Temp. (° C.) | catalyst | time (h) | [CH$_3$NH$_2$] (M) | 4-CPA (% conv.) | 5-DMPD (% yield) | 5-MPPD (% yield) | 2-MGA (% yield) |
|---|---|---|---|---|---|---|---|
| 160 | 5% Pd/C | 2 | 1.0 | 100 | 53.5 | 0 | 0.7 |
| 160 | 5% Pd/C | 2 | 1.25 | 100 | 68.3 | 0 | 0.8 |

-continued

| Temp. (° C.) | catalyst | time (h) | [CH$_3$NH$_2$] (M) | 4-CPA (% conv.) | 5-DMPD (% yield) | 5-MPPD (% yield) | 2-MGA (% yield) |
|---|---|---|---|---|---|---|---|
| 160 | 5% Pd/C | 2 | 1.5 | 100 | 76.4 | 0 | 0.9 |
| 160 | 5% Pd/C | 2 | 2.0 | 100 | 81.5 | 0 | 1.8 |
| 160 | 5% Pd/C | 2 | 3.0 | 99 | 81.7 | 7.8 | 3.3 |
| 160 | 5% Pd/C | 2 | 4.0 | 99 | 88.4 | 1.9 | 2.6 |

EXAMPLE 41

1,5-Dimethyl-2-Piperidone from 4-Cyanopentanoic Acid Ammonium Salt

Hydrogenations of 5-mL aqueous reaction mixtures containing 1.0 M 4-cyanopentanoic acid ammonium salt (filtered product mixture from Example 9, reaction #5), from 3.0 M to 4.0 M methylamine, and 5 wt. % (relative to weight of 4-cyanopentanoic acid) of either 5% palladium on carbon or 4.5% palladium/0.5% platinum on carbon were run in glass shaker tubes at 500 psig hydrogen gas and at 180° C. for 2 h, then analyzed for the production of 1,5-dimethyl-2-piperidone (5-DMPD), 5-methyl-2-piperidone (5-MPPD), and 2-methylglutaric acid (2-MGA):

| Temp. (° C.) | catalyst | [CH$_3$NH$_2$] (M) | 4-CPA (% conv.) | 5-DMPD (% yield) | 5-MPPD (% yield) | 2-MGA (% yield) |
|---|---|---|---|---|---|---|
| 180 | 5% Pd/C | 3.0 | 97 | 73.0 | 6.6 | — |
| 180 | 4.5% Pd/ 0.5% Pt/C | 3.0 | 96 | 69.0 | 1.9 | 23.9 |
| 180 | 5% Pd/C | 4.0 | 95 | 66.6 | 2.6 | 33.5 |

EXAMPLE 42

1,5-Dimethyl-2-Piperidone from 4-Cyanopentanoic Acid Ammonium Salt

Into a 100 mL graduated cylinder was placed 54.4 mL of an aqueous reaction mixture containing 1.84 M 4-cyanopentanoic acid ammonium salt (0.1 mole 4-cyanopentanoic acid ammonium salt, produced by the enzymatic hydrolysis of 2-methylglutaronitrile; Example 9, filtered product mixture from reaction #5), then 25.8 ml of 40 wt. % methylamine (9.31 g methylamine, 0.3 mole) was added and the final volume adjusted to 100 mL with distilled water. The final concentrations of 4-cyanopentanoic acid ammonium salt and methylamine were 1.0 M and 3.0 M, respectively. To the resulting solution was added 0.636 g (5 wt. %/wt. of 4-cyanopentanoic acid) of 5% Pd on carbon powder, and the resulting mixture charged to a 300-mL 314 SS Autoclave Engineers EZE-Seal stirred autoclave equipped with a Dispersimax® turbine-type impeller. After flushing the reactor with nitrogen, the contents of the reactor were stirred at 1000 rpm and heated at 160° C. under 500 psig of hydrogen gas for 4 h. Samples (ca. 1.5 mL) were removed via a sampling tube over the course of the reaction for analysis. After cooling to room temperature, analysis of the final reaction mixture by gas chromatography indicated a 72.8% yield of 1,5-dimethyl-2-piperidone, 3.5% 5-methyl-2-piperidone, 19.9% 2-methylglutaric acid, and no 4-cyanopentanoic acid ammonium salt remaining.

The product mixture (61 mL after sampling) was filtered to remove the catalyst, then adjusted to pH 7.0 with 6 N HCl and saturated with sodium chloride. The resulting solution was extracted four times with 100 mL of ethyl ether, and the combined organic extracts dried over magnesium sulfate, filtered, and the solvent removed by rotary evaporation under reduced pressure to yield a colorless liquid. This liquid was distilled at 3.5 Torr and the fraction boiling at 70.0–71.5° C. collected to yield 4.65 g (60% isolated yield) of 1,5-dimethyl-2-piperidone (5-DMPD).

EXAMPLE 43

4-Ethyl-1-Methylpyrrolidin-2-One from 3-Cyanopentanoic Acid Ammonium Salt

Into a 100 mL graduated cylinder was placed 79.4 mL of an aqueous reaction mixture containing 1.26 M 3-cyanopentanoic acid ammonium salt (0.1 mole 3-cyanopentanoic acid ammonium salt, produced by the enzymatic hydrolysis of 2-ethylsuccinonitrile; Example 13 filtered product mixture), then 17.2 mL of 40 wt. % methylamine (6.21 g methylamine, 0.2 mole) was added and the final volume adjusted to 100 mL with distilled water. The final concentrations of 3-cyanopentanoic acid ammonium salt and methylamine were 1.0 M and 2.0 M, respectively. To the resulting solution was added 0.636 g (5 wt. %/wt. of 3-cyanopentanoic acid) of 5% Pd on carbon powder, and the resulting mixture charged to a 300-mL 314 SS Autoclave Engineers EZE-Seal stirred autoclave equipped with a Dispersimax® turbine-type impeller. After flushing the reactor with nitrogen, the contents of the reactor were stirred at 1000 rpm and heated at 140° C. under 500 psig of hydrogen gas for 4 h. Samples (ca. 1.5 mL) were removed via a sampling tube over the course of the reaction for analysis. After cooling to room temperature, analysis of the final reaction mixture by gas chromatography indicated a 69.8% yield of 4-ethyl-1-methylpyrrolidin-2-one and a 20.4% yield of 4-ethylpyrrolidin-2-one, with no 3-cyanopentanoic acid ammonium salt remaining.

The product mixture (80 mL after sampling) was filtered to remove the catalyst, then adjusted to pH 7.0 with 6 N HCl and saturated with sodium chloride. The resulting solution was extracted four times with 100 mL of dichloro-methane, and the combined organic extracts dried over magnesium sulfate, filtered, and the solvent removed by rotary evaporation under reduced pressure to yield a colorless liquid. This liquid was fractionally-distilled at 16 Torr, and the fraction boiling at 100° C. was collected (5.15 g, 51% yield). The resulting 4-ethyl-1-methylpyrrolidin-2-one contained <5% 4-ethylpyrrolidin-2-one as impurity, so the liquid was redistilled at 40 Torr and the fraction boiling at 128° C. collected to yield 3.71 g (37% isolated yield) of 4-ethyl-1-methylpyrrolidin-2-one (4-EMPRD).

EXAMPLE 44

5-Methyl-2-Piperidone from 4-Cyano-4-Pentenoic Acid Ammonium Salt

Into a 100 mL graduated cylinder was placed 77.0 mL of an aqueous reaction mixture containing 1.30 M 4-cyano-4-pentenoic acid ammonium salt (0.1 mole 4-cyanopentanoic acid ammonium salt, produced by the enzymatic hydrolysis of 2-methyleneglutaronitrile; Example 17), then 12.9 mL of concentrated ammonium hydroxide (29.3% $NH_3$, 0.2 mole $NH_3$) was added and the final volume adjusted to 100 mL with distilled water. The final concentrations of 4-cyano-4-pentenoic acid ammonium salt and added ammonium hydroxide were 1.0 M and 2.0 M, respectively. To the resulting solution was added 0.626 g (5 wt. %/wt. of 4-cyano-4-pentenoic acid) of chromium-promoted Raney Nickel (Grace Davison Raney® 2400 Active Metal Catalyst), and the resulting mixture charged to a 300-mL 314 SS Autoclave Engineers EZE-Seal stirred autoclave equipped with a Dispersimax® turbine-type impeller. After flushing the reactor with nitrogen, the contents of the reactor were stirred at 1000 rpm and heated under 500 psig of hydrogen gas at 50° C. for 5 h, then for an additional 3 h at 160° C. After cooling to room temperature, analysis of the final reaction mixture by gas chromatography indicated a 85.0% yield of 5-methyl-2-piperidone, with no 4-cyano-4-pentenoic acid ammonium salt remaining.

EXAMPLE 45

2-Pyrrolidinone from 3-Cyanopropionic Acid Ammonium Salt

Into a 100 mL graduated cylinder was placed 75.8 mL of an aqueous reaction mixture containing 1.31 M 3-cyanopropionic acid ammonium salt (0.1 mole 3-cyanopropionic acid ammonium salt, produced by the enzymatic hydrolysis of succinonitrile; Example 20), then 19.4 mL of concentrated ammonium hydroxide (29.3% $NH_3$, 0.3 mole NH3) was added and the final volume adjusted to 100 mL with distilled water. The final concentrations of 3-cyanopropionic acid ammonium salt and added ammonium hydroxide were 1.0 M and 3.0 M, respectively. To the resulting solution was added 0.99 g (10 wt. %/wt. of 3-cyanopropionic acid) of chromium-promoted Raney Nickel (Grace Davison Raney® 2400 Active Metal Catalyst), and the resulting mixture charged to a 300-mL 314 SS Autoclave Engineers EZE-Seal stirred autoclave equipped with a Dispersimax® turbine-type impeller. After flushing the reactor with nitrogen, the contents of the reactor were stirred at 1000 rpm and heated under 500 psig of hydrogen gas at 70° C. for 4.5 h, then for an additional 5 h at 180° C. Analysis by gas chromatography indicated a 91.0% yield of 2-pyrrolidinone, with no 3-cyanopropionic acid ammonium salt remaining.

EXAMPLE 46

2-Piperidone from 4-Cyanobutyric Acid Ammonium Salt

The procedure described in Example 22 was repeated. After 4.0 h, the HPLC yield of 4-cyanobutyric acid ammonium salt and glutaric acid diammonium salt was 91.7% and 7.5%, respectively, with no glutaronitrile remaining. The final concentration of 4-cyanobutyric acid ammonium salt in the centrifuged and filtered reaction mixture was 1.42 M. Into a 100 mL graduated cylinder was placed 70.6 mL (0.100 mole of 4-cyanobutyric acid ammonium salt) of the filtered aqueous reaction mixture, then 19.4 mL of concentrated ammonium hydroxide (29.3% $NH_3$, 0.3 mole NH3) was added and the final volume adjusted to 100 mL with distilled water. The final concentrations of 4-cyanopropionic acid ammonium salt and added ammonium hydroxide were 1.0 M and 3.0 M, respectively. To the resulting solution was added 1.13 g (10 wt. %/wt. of 4-cyanobutyric acid) of chromium-promoted Raney Nickel (Grace Davison Raney® 2400 Active Metal Catalyst), and the resulting mixture charged to a 300-mL 314 SS Autoclave Engineers EZE-Seal stirred autoclave equipped with a Dispersimax® turbine-type impeller. After flushing the reactor with nitrogen, the contents of the reactor were stirred at 1000 rpm and heated under 500 psig of hydrogen gas at 70° C. for 3.5 h. Analysis by gas chromatography indicated a 29.7% yield of 2-piperidone, with no 4-cyanobutyric acid ammonium salt remaining. The temperature was increased to 180° C. for an additional 2 h, and subsequent analysis of a sample by gas chromatography indicated a 93.5% yield of 2-pyrrolidinone.

EXAMPLE 47

5-Methyl-2-Piperidone from 4-Cyanopentanoic Acid Ammonium Salt

Fifty milliliters of an aqueous mixture containing 1.85 M 4-cyanopentanoic acid ammonium salt (0.1 mole 4-cyanopentanoic acid ammonium salt, produced by the enzymatic hydrolysis of 2-methylglutaronitrile; Example 9, filtered product mixture from reaction #5), 5.6 g of 29% aqueous ammonium hydroxide and 44 mL D.I. water was charged to a 300 mL autoclave. To this solution was added 0.73 g (3 wt % based on 4-cyanopentanoic acid) of 4.5% Pd/0.5% Pt on carbon catalyst. The autoclave was sealed and purged 3 times with hydrogen followed by heating to 160° C. under 100 psig hydrogen and slow stirring. At 160° C., the pressure was raised to 800 psig and maximum stirring commenced. After 3 hours, the reactor was cooled, vented and purged with nitrogen. Gas chromatographic analysis of the product mixture indicated a 96% conversion of 4-cyanopentanoic acid and a 95.5% yield (99.5% selectivity) to 5-methyl-2-piperidone.

EXAMPLE 48

1,5-Dimethyl-2-Piperidone from 4-Cyanopentanoic Acid Ammonium Salt

One hundred milliliters of an aqueous mixture containing 1.85 M 4-cyanopentanoic acid ammonium salt (0.2 mole 4-cyanopentanoic acid ammonium salt, produced by the enzymatic hydrolysis of 2-methylglutaronitrile; Example 9, filtered product mixture from reaction #5), and 14 g (0.2 mole) 40% aqueous methylamine was charged to a 300 mL autoclave. To this solution was added 4.5% Pd/0.5% Pt on carbon catalyst. The autoclave was sealed and purged 3 times with hydrogen followed by heating to reaction under 100 psig hydrogen and slow stirring. At reaction temperature, the pressure was raised and maximum stirring commenced. After a given reaction time, the reactor was cooled, vented and purged with nitrogen. Gas chromatographic analysis of the product mixture for several runs at different reaction conditions are summarized below:

| Temp. (° C.) | $H_2$ (psig) | catalyst loading (wt %) | time (h) | 4-CPA (% conv.) | 5-DMPD (% yield) | 5-MPPD (% yield) |
|---|---|---|---|---|---|---|
| 175 | 300 | 7.4 | 3 | 99 | 67.8 | 28.2 |
| 160 | 500 | 10 | 2 | 99 | 68.6 | 28.1 |
| 145 | 500 | 10 | 2 | 93 | 65.2 | 26.4 |

EXAMPLE 49

1,5-Dimethyl-2-Piperidone from 4-Cyanopentanoic Acid Ammonium Salt

Hydrogenations of 4-cyanopentanoic acid ammonium salt were performed in 5 mL glass shaker tubes at 800 psig using different Pd on carbon catalysts. Four milliliters of 1.85 M (7 mmoles) aqueous 5-cyanopentanoic acid (filtered product mixture from Example 9, reaction #5), 0.88 g (11.4 mmoles) 40% methylamine and catalyst from a group consisting of 5% Pd/C and 4.5% Pd/0.5% Pt/C were charged to the tube and run for 3 hours. Gas chromatographic analysis of the product mixtures, after cooling to 25°, at different reaction conditions are summarized below:

| Temp. (° C.) | catalyst | catalyst loading (wt %) | time (h) | 4-CPA (% conv.) | 5-DMPD (% yield) | 5-MPPD (% yield) |
|---|---|---|---|---|---|---|
| 160 | 5% Pd/C | 1.2 | 2 | 99 | 91.8 | 5.0 |
| 160 | 4.5% Pd 0.5% Pt/C | 0.7 | 2 | 99 | 94.0 | 3.1 |
| 150 | 5% Pd/C | 0.7 | 2 | 99 | 92.5 | 2.2 |

We claim:
1. Isolated microorganisms characterized by an aliphatic nitrilase activity and selected from the group consisting of *Acidovorax facilis* 72W (ATCC 55746), *Acidovorax facilis* 72-PF-15 (ATCC 55747), *Acidovorax facilis* 72-PF-17 (ATCC 55745).

* * * * *